United States Patent
Kondo

(10) Patent No.: US 10,123,763 B2
(45) Date of Patent: Nov. 13, 2018

(54) X-RAY CT SYSTEM

(71) Applicant: Toshiba Medical Systems Corporation, Otawara-shi (JP)

(72) Inventor: Gen Kondo, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/712,234

(22) Filed: May 14, 2015

(65) Prior Publication Data

US 2015/0289834 A1  Oct. 15, 2015

Related U.S. Application Data

(63) Continuation of application No. PCT/JP2013/080710, filed on Nov. 13, 2013.

(30) Foreign Application Priority Data

Nov. 14, 2012  (JP) .................. 2012-249812
Nov. 13, 2013  (JP) .................. 2013-234596

(51) Int. Cl.
*A61B 6/00* (2006.01)
*A61B 6/02* (2006.01)
(Continued)

(52) U.S. Cl.
CPC .............. *A61B 6/548* (2013.01); *A61B 6/027* (2013.01); *A61B 6/032* (2013.01); *A61B 6/035* (2013.01);
(Continued)

(58) Field of Classification Search
CPC ......... A61B 6/027; A61B 6/032; A61B 6/035; A61B 6/0407; A61B 6/461; A61B 6/507;
(Continued)

(56) References Cited

U.S. PATENT DOCUMENTS 5,224,135 A * 6/1993 Toki ............... A61B 6/032
378/15
5,694,449 A 12/1997 Aragones
(Continued)

FOREIGN PATENT DOCUMENTS

CN 101401727 A 4/2009
JP H10-043170 A 2/1998
(Continued)

OTHER PUBLICATIONS

International Search Report dated Dec. 17, 2013 for PCT/JP2013/080710 filed on Nov. 13, 2013 in English Language.
(Continued)

*Primary Examiner* — Irakli Kiknadze
(74) *Attorney, Agent, or Firm* — Oblon, McClelland, Maier & Neustadt, L.L.P.

(57) ABSTRACT

An X-ray CT system of an embodiment includes an X-ray scanner including an X-ray generator that performs X-ray imaging by scanning around a subject that is placed on a bed top and an X-ray detector. The X-ray scanner performs X-ray imaging while the bed top and the X-ray scanner are being reciprocated relative to each other in a first direction along the longitudinal direction of the bed top and a second direction opposite thereto. The X-ray CT system further includes a comparator that compares the positions of the bed top when a predetermined number of views are acquired in a plurality of times of X-ray imaging in the first direction or in a plurality of times of X-ray imaging in the second direction.

14 Claims, 12 Drawing Sheets

(51) Int. Cl.
*A61B 6/03* (2006.01)
*A61B 6/04* (2006.01)

(52) U.S. Cl.
CPC ............ *A61B 6/0407* (2013.01); *A61B 6/461* (2013.01); *A61B 6/507* (2013.01); *A61B 6/54* (2013.01)

(58) Field of Classification Search
CPC .......... A61B 6/54; A61B 6/548; A61B 6/037; A61B 6/5235; A61B 6/00; A61B 6/4275; A61B 6/4417; A61B 6/4476; A61B 6/466; A61B 6/04; A61B 6/0457; A61B 6/4405; A61B 6/4441; A61B 6/508; A61B 6/107; A61B 5/0031; A61B 6/08; A61B 6/40; A61B 6/542; A61B 6/589; A61B 6/4464; A61B 6/541; A61B 6/06; A61B 6/547; A61B 6/03; A61B 6/4258; A61B 6/4291; A61B 6/488; G06T 11/005; G06T 2211/432; G06T 11/006; G06T 2211/421; G01T 1/2985; G06F 19/321; G06F 19/3487; G01N 2223/419; G01N 2223/612; G01N 23/046; G01R 33/543; G01R 33/546; G06Q 10/10; G06Q 50/22; G06Q 50/02
USPC .......................................... 378/4, 19, 20, 205
See application file for complete search history.

(56) References Cited

U.S. PATENT DOCUMENTS

| | | | |
|---|---|---|---|
| 6,851,851 B2 * | 2/2005 | Smith | A61B 6/0457 378/167 |
| 2003/0068005 A1 * | 4/2003 | Yamazaki | A61B 6/032 378/4 |
| 2005/0267349 A1 * | 12/2005 | Goto | G06F 19/321 600/407 |
| 2008/0152076 A1 | 6/2008 | Hagiwara | |
| 2009/0092224 A1 | 4/2009 | Nishide et al. | |
| 2009/0166541 A1 * | 7/2009 | Tsuchiya | G01T 1/1648 250/363.05 |
| 2009/0189079 A1 | 7/2009 | Ohta et al. | |
| 2011/0069810 A1 | 3/2011 | Kondo | |
| 2013/0251101 A1 * | 9/2013 | Saito | A61B 6/547 378/20 |
| 2013/0266117 A1 * | 10/2013 | Ooshima | A61B 6/0407 378/20 |

FOREIGN PATENT DOCUMENTS

| | | |
|---|---|---|
| JP | 2001-120539 A | 5/2001 |
| JP | 2007-236777 | 9/2007 |
| JP | 2008-142354 A | 6/2008 |
| JP | 2009-089760 A | 4/2009 |
| JP | 2009-180519 A | 8/2009 |
| JP | 2011-062445 A | 3/2011 |
| WO | WO 2010/047380 A1 | 4/2010 |

OTHER PUBLICATIONS

Combined Chinese Office Action and Search Report dated Feb. 4, 2017 in Chinese Patent Application No. 201380059447.X (with English translation of categories of cited documents).

* cited by examiner

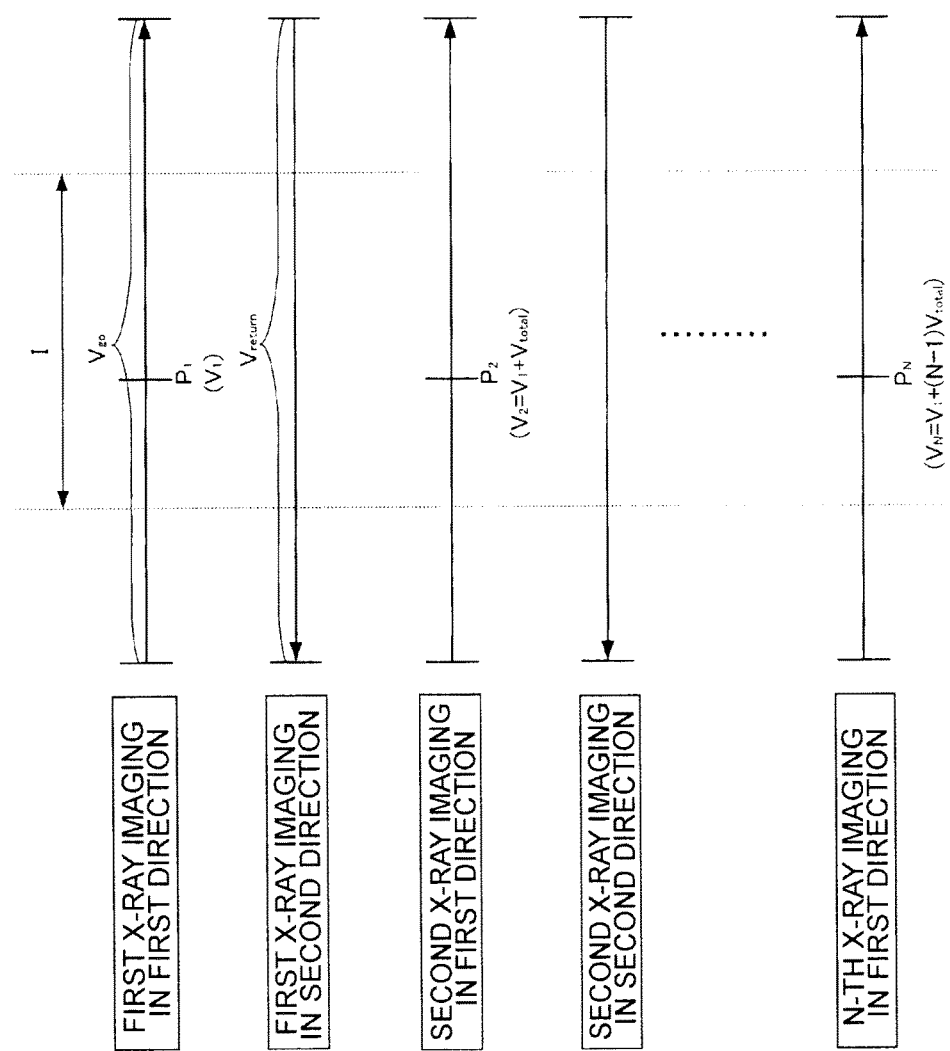

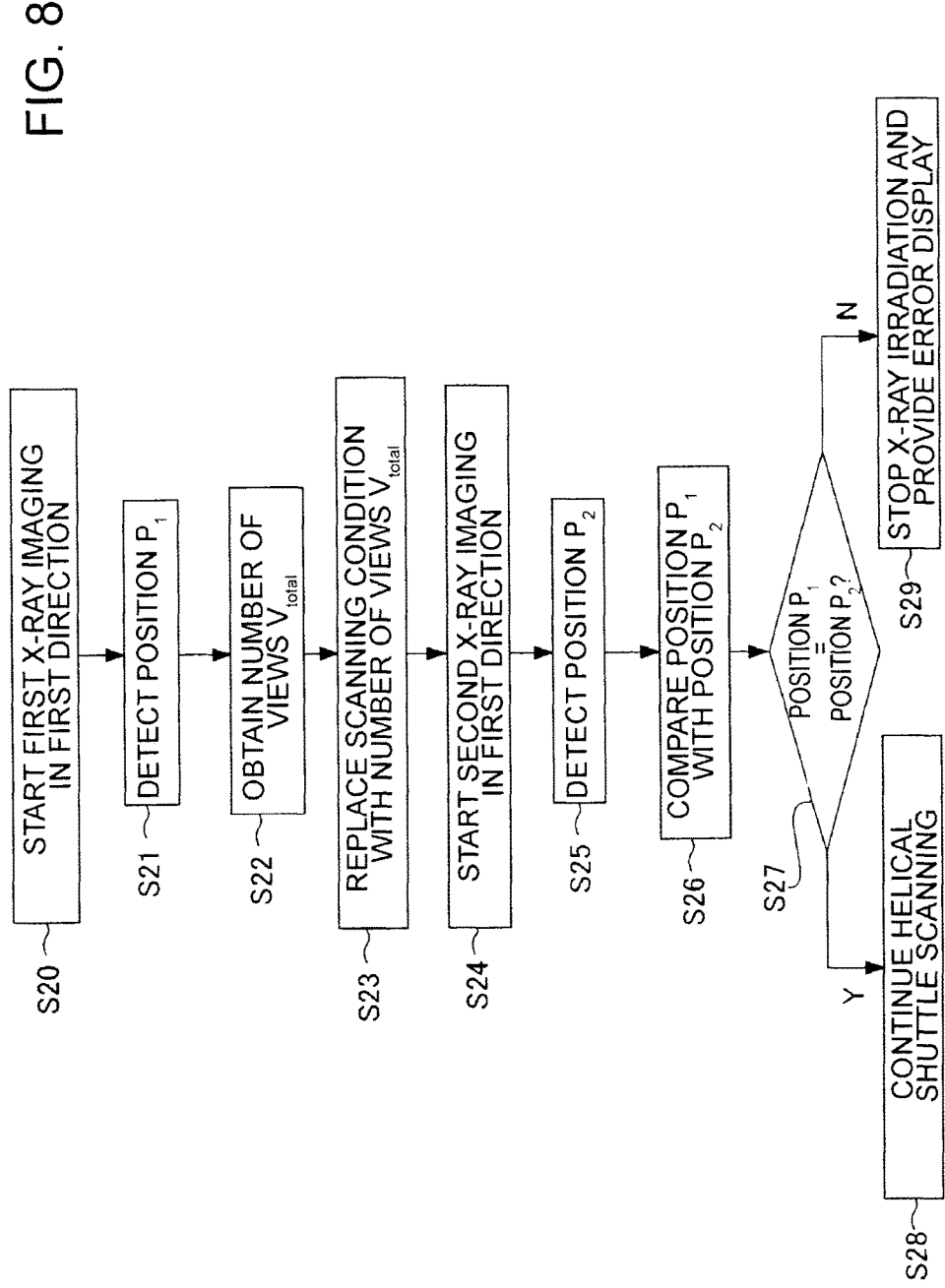

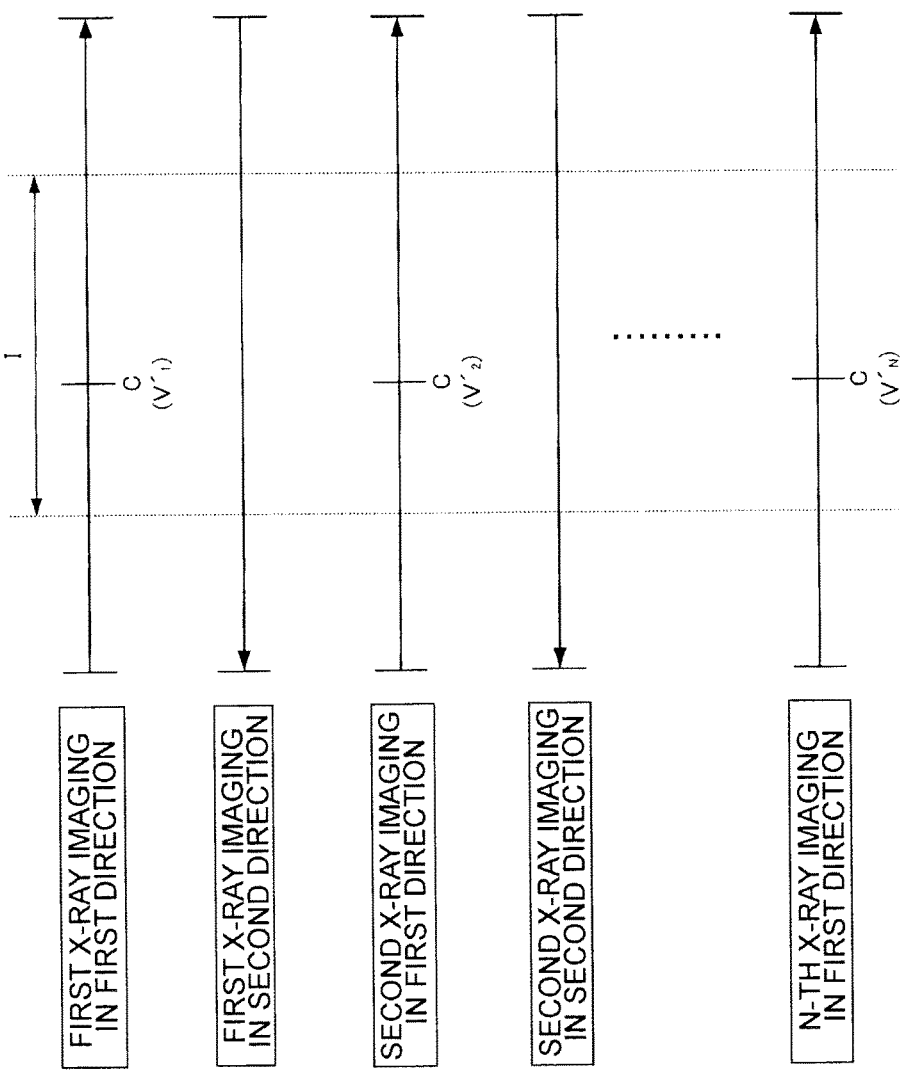

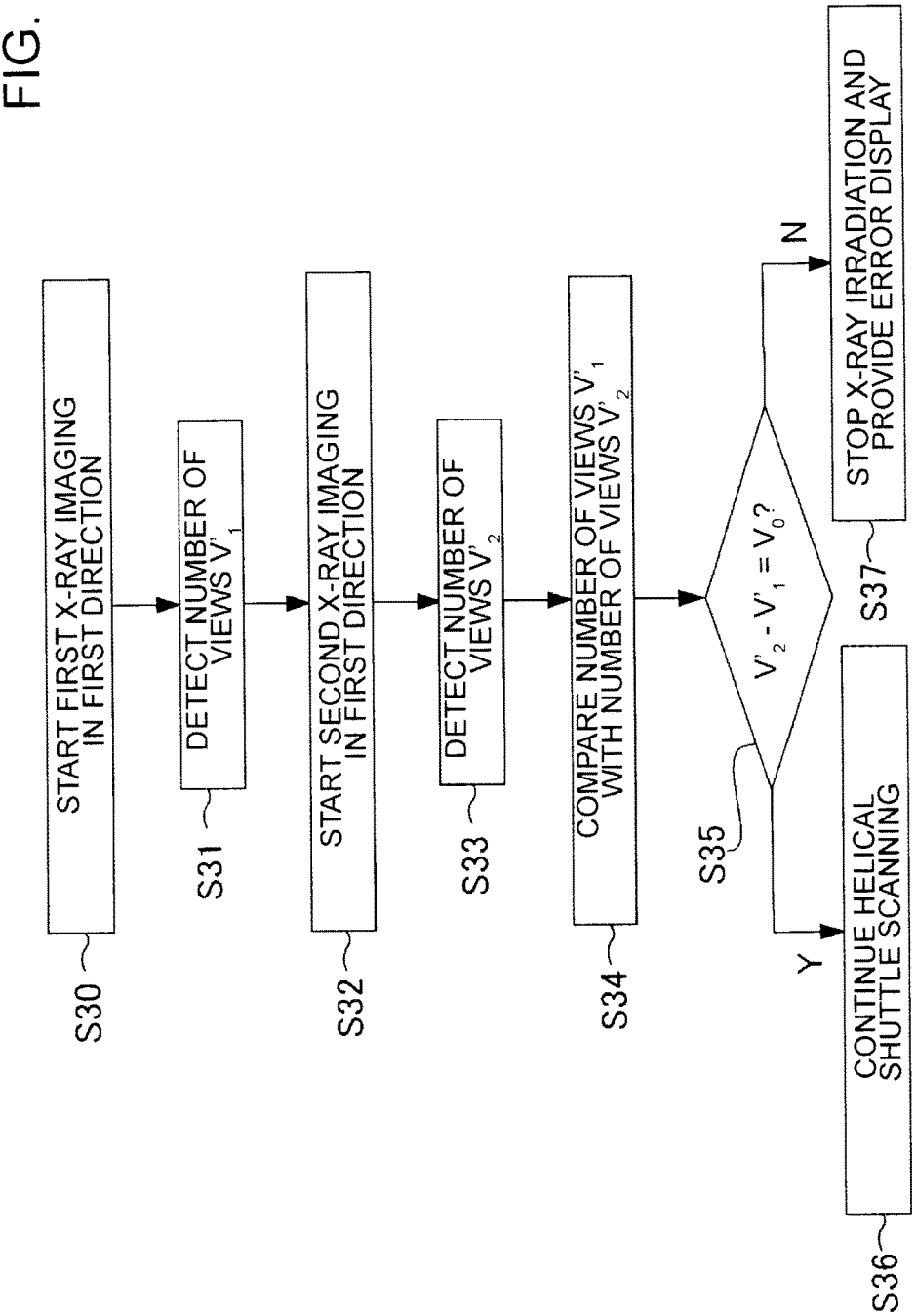

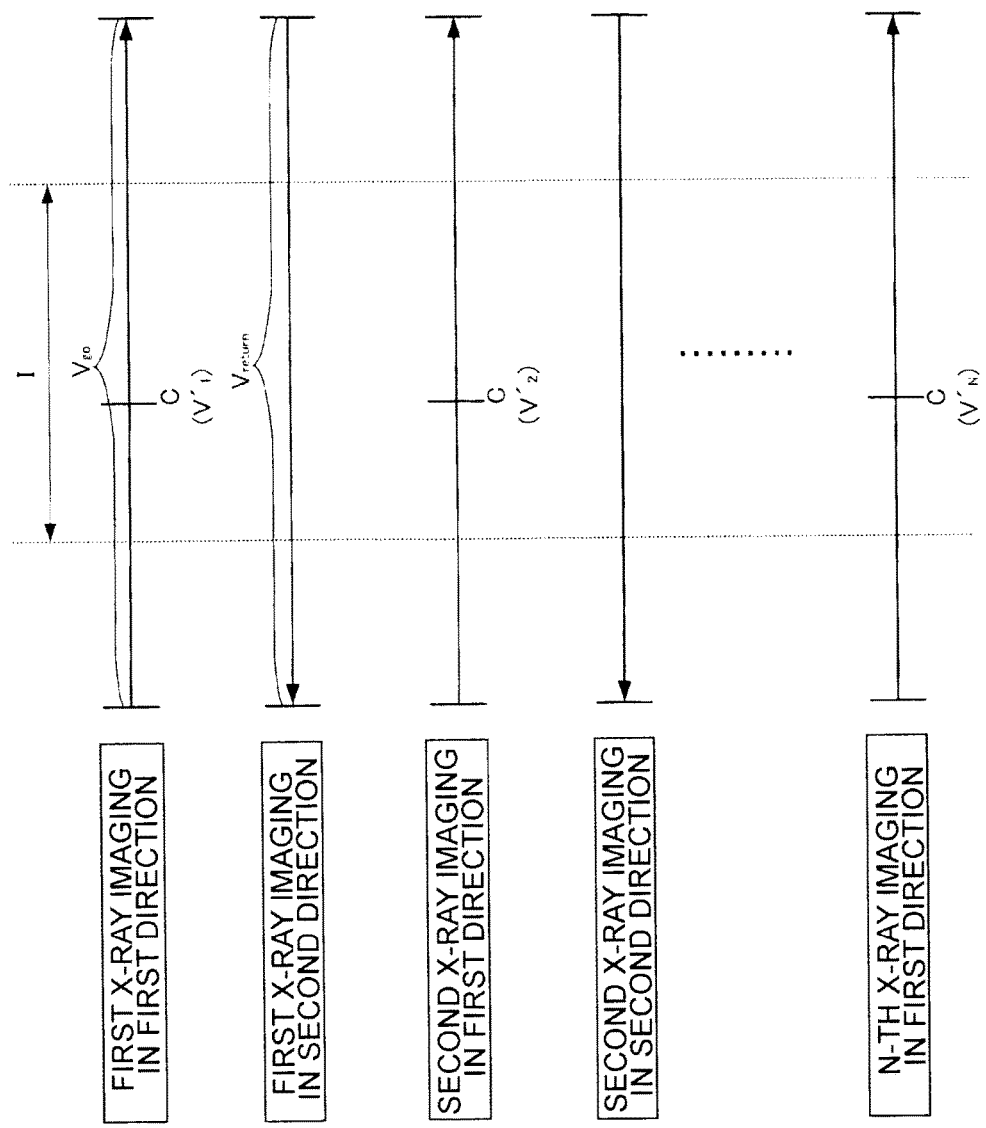

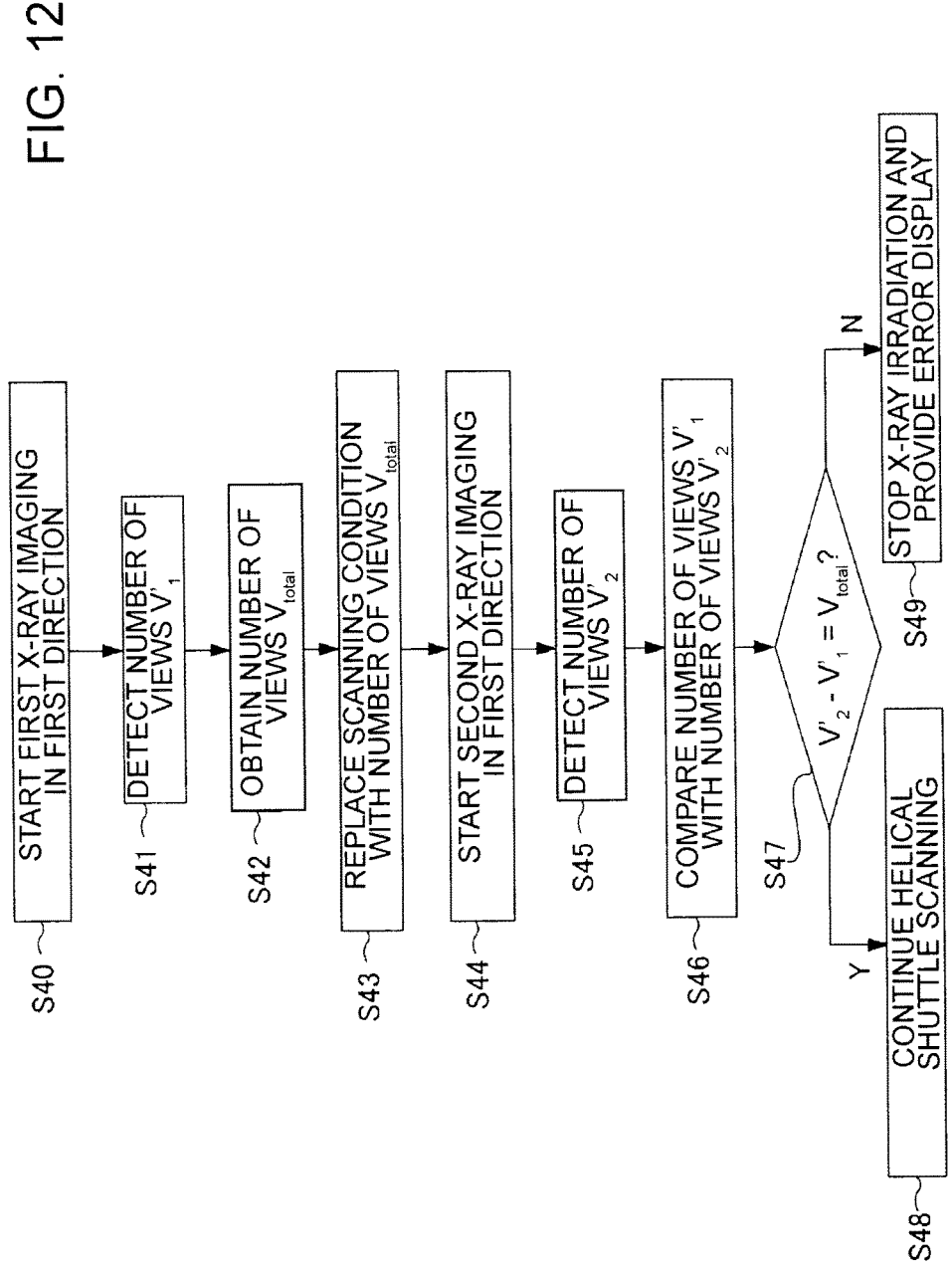

X-RAY CT SYSTEM

CROSS-REFERENCE TO RELATED APPLICATION

This application is based upon and claims the benefit of priority from Japanese Patent Application No. 2012-249812, filed 14 Nov. 2012 and Japanese Patent Application No. 2013-234596, filed 13 Nov. 2013; the entire contents of which are incorporated herein by reference.

FIELD

Embodiments described herein relate generally to an X-ray CT system.

BACKGROUND

An X-ray computed tomography (CT) system is a device that scans a subject with X-rays and processes collected data by a computer to create an image of the inside of the subject.

Specifically, the X-ray CT system irradiates the subject with X-rays a plurality of times from different directions through an X-ray generator, and detects X-rays having passed through the subject by a plurality of X-ray detecting elements. A data acquisition unit collects detection data. After the A/D conversion of the detection data thus collected, the data acquisition unit sends the data to a console device. The console device performs preprocessing and the like on the detection data and thereby generates projection data. The console device then performs reconstruction processing based on the projection data, and creates tomographic image data or volume data based on a plurality of tomographic image data.

Helical shuttle scanning is a scanning method using an X-ray CT system. In helical shuttle scanning, helical scan (scanning by irradiating a subject with X-rays in a spiral pattern) is performed on an imaging range that includes a range corresponding to the region of interest (ROI) of the subject while a bed top on which the subject is placed is being reciprocated in the first direction and in a direction opposite to the first direction (second direction). Tomographic image data based on detection data in the first direction and the second direction acquired by the helical shuttle scanning is used for, for example, CT perfusion. CT perfusion is a technique for superimposing CT images obtained by a plurality of times of X-ray imaging of the same location. For example, an image obtained by CT perfusion is used to represent changes in contrast-enhanced cerebral blood flow by gradation to analyze the symptoms of ischemia or the like.

To superimpose a plurality of CT images as described above, in helical shuttle scanning, the trajectory of X-rays irradiated spirally to the subject is controlled to synchronize between scan in the first direction (hereinafter, sometimes referred to as "forward scan") and scan in the second direction (hereinafter, sometimes referred to as "backward scan"). Thus, in any of the forward scan and the backward scan, the X-ray generator starts irradiation of X-rays using a position on the circular trajectory as a base point (start point). Scans of different timings, in which X-ray irradiation (and the movement of the bed top) always starts from the same position, are referred to as synchronous trajectory scan.

When CT perfusion is performed by superposing a plurality of CT images, forward scan (backward scan) has to be repeated a plurality of times under the same conditions (the position of the bed top, the number of detection data (views) to be acquired, etc.). In other words, the reproducibility of the scan is required.

If the reproducibility of the scan is poor, there may be a difference between the number of views acquired by the first forward scan and that obtained by the second forward scan. This may cause misalignment in CT images generated based on detection data obtained by the scans when the images are superimposed. As a result, it may be difficult to accurately analyze the symptoms of ischemia or the like. If misalignment has occurred in a range corresponding to the region of interest (ROI) of the subject, the effect becomes larger. In addition, since such CT images are not suitable for CT perfusion, another helical shuttle scanning is required. This leads to an increase in X-ray radiation exposure.

BRIEF DESCRIPTION OF THE DRAWINGS

FIG. 7 is a diagram for supplementing the explanation of a monitoring unit according to a second embodiment;

FIG. 8 is a flowchart of an outline of the operation of an X-ray CT system of the second embodiment;

FIG. 9 is a diagram for supplementing the explanation of a monitoring unit according to a third embodiment;

FIG. 10 is a flowchart of an outline of the operation of an X-ray CT system of the third embodiment;

FIG. 11 is a diagram for supplementing the explanation of a monitoring unit according to a fourth embodiment; and FIG. 12 is a flowchart of an outline of the operation of an X-ray CT system of the fourth embodiment.

DETAILED DESCRIPTION

In general, according to one embodiment, an X-ray CT system includes an X-ray scanner including an X-ray generator that performs X-ray imaging by scanning around a subject that is placed on a bed top and an X-ray detector. The X-ray scanner performs X-ray imaging while the bed top and the X-ray scanner are being reciprocated relative to each other in a first direction along the longitudinal direction of the bed top and a second direction opposite thereto. The X-ray CT system further includes a comparator that compares the positions of the bed top when a predetermined number of views are acquired in a plurality of times of X-ray imaging in the first direction or in a plurality of times of X-ray imaging in the second direction.

First Embodiment

Referring now to FIGS. 1 to 6, a description is given of the configuration of an X-ray CT system 1 according to a first embodiment.

<System Configuration>

Figure 1:
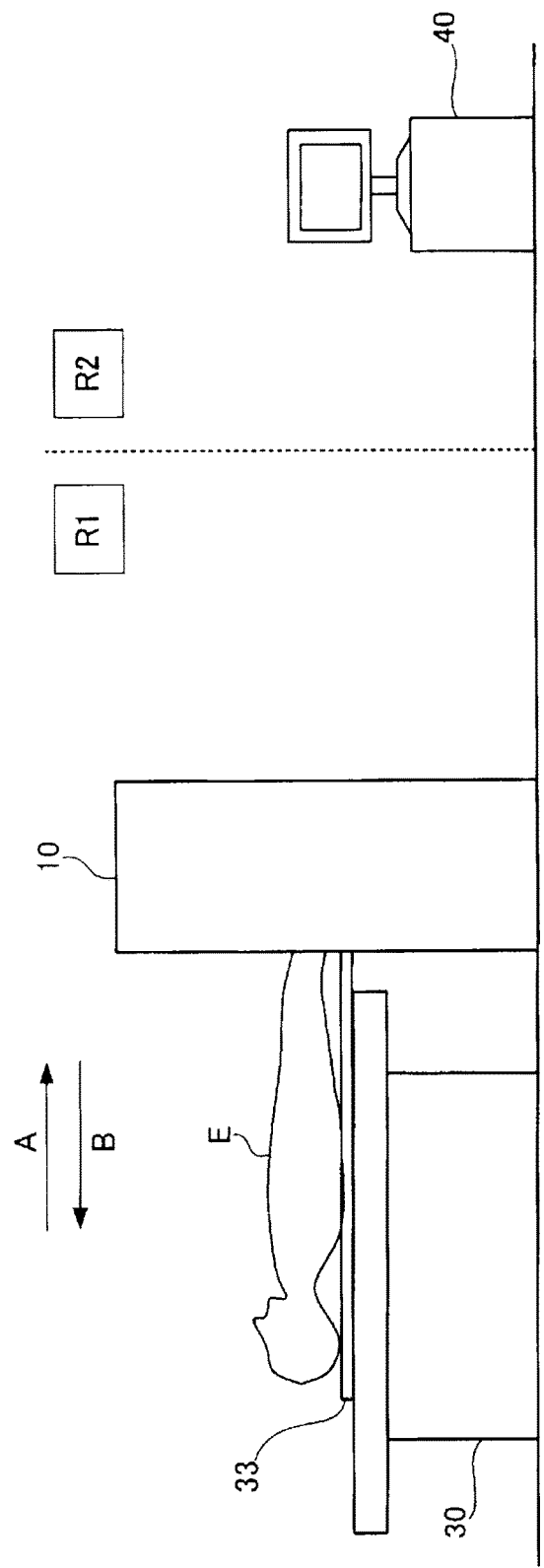
FIG. 1 is an overall view of an X-ray CT system according to a first embodiment.
Figure 2:
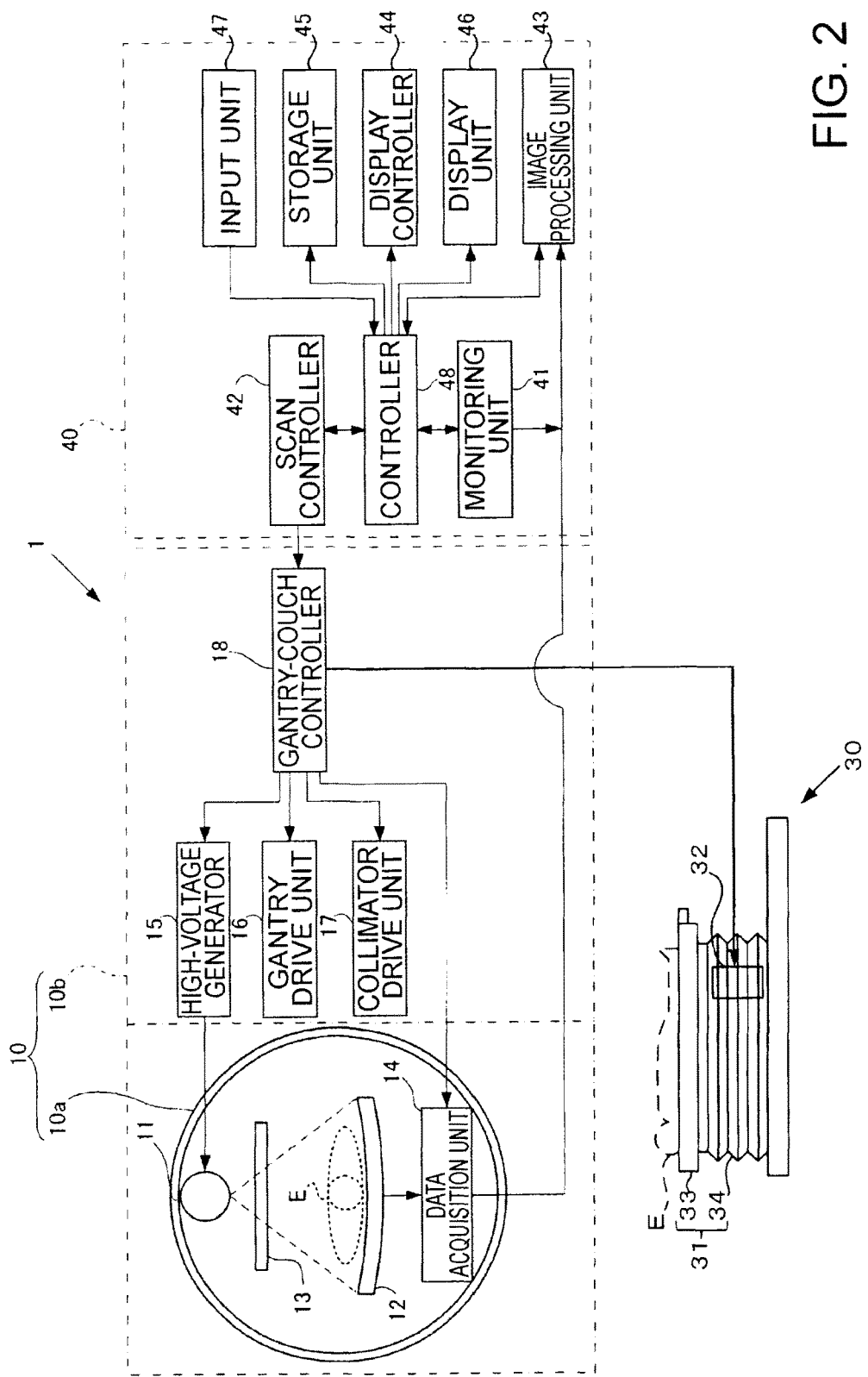
FIG. 2 is a block diagram of the X-ray CT system of the first embodiment.

FIG. 1 is an overall view of the X-ray CT system 1. FIG. 2 is a block diagram of the configuration of the X-ray CT system 1. The X-ray CT system 1 includes a gantry device 10, a couch device 30, and a console device 40.

As illustrated in FIG. 1, the gantry device 10 and the couch device 30 are located in an examination room R1. The console device 40 is located in a room R2 other than the examination room (in FIG. 1, a dashed line indicates the boundary between the examination room R1 and the room R2).

In the embodiment, an example is described in which a bed top 33 (described later) on which a subject E is placed is reciprocated in a first direction (forward direction indicated by arrow A) and a second direction opposite thereto (backward direction indicated by arrow B) with respect to the gantry device 10. The first direction and the second direction are along the longitudinal direction of the bed top 33. The first direction may be the backward direction, and the second direction may be the forward direction.

[Gantry Device]

The gantry device 10 irradiates the subject E with X-rays and collects detection data of X-rays that have passed through the subject E. The gantry device 10 includes a rotating portion 10a and a fixed portion 10b.

The rotating portion 10a includes an X-ray generator 11, an X-ray detector 12, an X-ray collimator 13, and a data acquisition unit 14.

The rotating portion 10a is a member for supporting the X-ray generator 11, the X-ray detector 12, and the like. The rotating portion 10a supports the X-ray generator 11 and the X-ray detector 12 so that they face each other across the subject E. In the gantry device 10, the rotating portion 10a rotates in a circular trajectory about the subject E.

The X-ray generator 11 includes an X-ray tube for generating X-rays (e.g., a tube for generating conical or pyramidal beams, not illustrated). The X-rays generated are irradiated to the subject E.

The X-ray detector 12 includes a plurality of X-ray detecting elements (not illustrated). The X-ray detector 12 detects X-ray intensity distribution data (hereinafter, sometimes referred to as "detection data") indicating the intensity distribution of X-rays that have passes through the subject E with the X-ray detecting elements, and outputs the detection data as a current signal. The X-ray detector 12 may be, for example, a two-dimensional X-ray detector (area detector) having a plurality of X-ray detecting elements arranged in two directions perpendicular to each other (a slice direction and a channel direction). The slice direction corresponds to the body axis direction of the subject E (directions indicated by arrows A and B in FIG. 1), while the channel direction corresponds to the rotational direction of the X-ray generator 11 (the X-ray detector 12). The X-ray generator 11 and the X-ray detector 12 in this embodiment are an example of "X-ray scanner". The X-ray scanner is capable of X-ray imaging by scanning around the subject E that is placed on the bed top 33.

The X-ray collimator 13 has a slit (opening) of a predetermined width. The width of the slit is changed to adjust the fan angle (spread angle in the channel direction) of X-rays irradiated from the X-ray generator 11 and the cone angle (spread angle in the slice direction) of the X-rays.

The data acquisition unit 14 (DAS: Data Acquisition System) collects detection data from the X-ray detector 12 (each X-ray detecting element). Further, the data acquisition unit 14 converts the collected detection data into digital data, and sends it to the console device 40 via the fixed portion 10b. In this embodiment, the data acquisition unit 14 associates detection data corresponding to one view with the position of the bed top 33 when the view is acquired, and sequentially sends it to the console device 40. In other words, views are in one-to-one correspondence with detection data. One view represents a range corresponding to a region of the X-ray detector 12 in which X-rays are detected when the X-rays are irradiated to the subject E from any position on the circular trajectory.

The fixed portion 10b holds the rotating portion 10a such that the portion 10a is rotatable with respect to the subject E. The fixed portion 10b includes a high-voltage generator 15, a gantry drive unit 16, a collimator drive unit 17, and a gantry-couch controller 18.

The high-voltage generator 15 applies a high voltage to the X-ray generator 11. The X-ray generator 11 generates X-rays based on the high voltage. The gantry drive unit 16 rotates the rotating portion 10a. The collimator drive unit 17 drives the X-ray collimator 13 to shape the X-rays generated by the X-ray generator 11 into a predetermined form.

The gantry-couch controller 18 controls the operation of the gantry device 10 and the couch device 30 including the data acquisition unit 14, the high-voltage generator 15, the gantry drive unit 16, the collimator drive unit 17, and a couch drive unit 32 (described later) under the control of the console device 40 (a scan controller 42).

[Couch Device]

The couch device 30 is used to place and move the subject E to be imaged. The couch device 30 includes a couch 31 and the couch drive unit 32. The couch 31 includes the bed top 33 for accommodating the subject E and a base 34 that supports the bed top 33. The bed top 33 can be moved by the couch drive unit 32 in the body axis direction of the subject E and a direction perpendicular to the body axis direction. Specifically, the couch drive unit 32 is capable of inserting/extracting the bed top 33 where the subject E is lying in/from the rotating portion 10a. The base 34 is capable of moving the bed top 33 vertically (in directions perpendicular to the body axis direction of the subject E) through the couch drive unit 32.

[Console Device]

The console device 40 is used for operation input to the X-ray CT system 1. The console device 40 has a function of reconstructing CT image data (tomographic image data and volume data) representing the internal structure of the subject E from detection data collected by the gantry device 10 and the like. The console device 40 includes a monitoring unit 41, the scan controller 42, an image processing unit 43, a display controller 44, a storage unit 45, a display unit 46, an input unit 47, and a controller 48.

Based on the number of views corresponding to the detection data sent from the data acquisition unit 14, the monitoring unit 41 monitors the reproducibility of helical shuttle scanning. The configuration of the monitoring unit 41 is described in detail later.

Through the gantry-couch controller 18, the scan controller 42 controls various operations relating to X-ray scanning. For example, through the gantry-couch controller 18, the scan controller 42 controls the high-voltage generator 15 to apply a high voltage to the X-ray generator 11. The scan controller 42 controls the gantry drive unit 16 to rotate the rotating portion 10a through the gantry-couch controller 18. The scan controller 42 controls the collimator drive unit 17 to activate the X-ray collimator 13 through the gantry-couch controller 18. The scan controller 42 controls the couch drive unit 32 to move the couch 31 through the gantry-couch controller 18.

Further, the scan controller 42 of the embodiment controls X-ray irradiation by the X-ray scanner based on a signal from the monitoring unit 41 (described in detail later).

The image processing unit 43 performs various types of processing such as preprocessing, reconstruction, rendering on the detection data sent from the gantry device 10 (the data acquisition unit 14). For example, the image processing unit 43 performs preprocessing such as logarithmic conversion, offset correction, sensitivity correction, and beam hardening correction on the detection data obtained by the gantry device 10 (the X-ray detector 12), and creates projection data. Based on the projection data, the image processing unit 43 creates CT image data (tomographic image data and volume data). Further, the image processing unit 43 performs rendering of the volume data, and creates a multi-planar reconstruction (MPR) image.

The display controller 44 performs various controls relating to image display. For example, the display controller 44 performs control to display on the display unit 46 an MPR image created by the image processing unit 43 and the like.

Further, the display controller 44 of the embodiment displays an error message or the like on the display unit 46 based on a signal from the monitoring unit 41 (described in detail later).

The storage unit 45 includes a semiconductor memory device such as a random access memory (RAM), a read only memory (ROM), and the like. The storage unit 45 stores the detection data and the projection data, and also CT image data.

The display unit 46 includes any display device such as a liquid crystal display (LCD), a cathode ray tube (CRT) display, or the like.

The input unit 47 is used as an input device for performing various operations on the console device 40. The input unit 47 includes, for example, a keyboard, a mouse, a trackball, a joystick, and the like. Further, as the input unit 47, a graphical user interface (GUI) displayed on the display unit 46 may be used.

The controller 48 controls the overall operation of the X-ray CT system 1 by controlling the operation of the gantry device 10, the couch device 30, and the console device 40. For example, the controller 48 controls the scan controller 42 so that the gantry device 10 performs pre-scan and main scan, thereby collecting detection data. Further, the controller 48 controls the image processing unit 43 to perform various types of processing (preprocessing, reconstruction, MPR, etc.) on the detection data. Further, the controller 48 controls the display controller 44 to display a CT image on the display unit 46 based on image data or the like stored in the storage unit 45.

In this embodiment, the controller 48 exerts control to perform helical shuttle scanning. That is, while relatively reciprocating the bed top 33 in the first direction along the longitudinal direction of the bed top 33 and in the second direction opposite thereto in an imaging range including a range corresponding to the region of interest of the subject E, the controller 48 controls the X-ray scanner to perform X-ray imaging in the position where it is moved to.

[Helical Shuttle Scanning]

Figure 3:
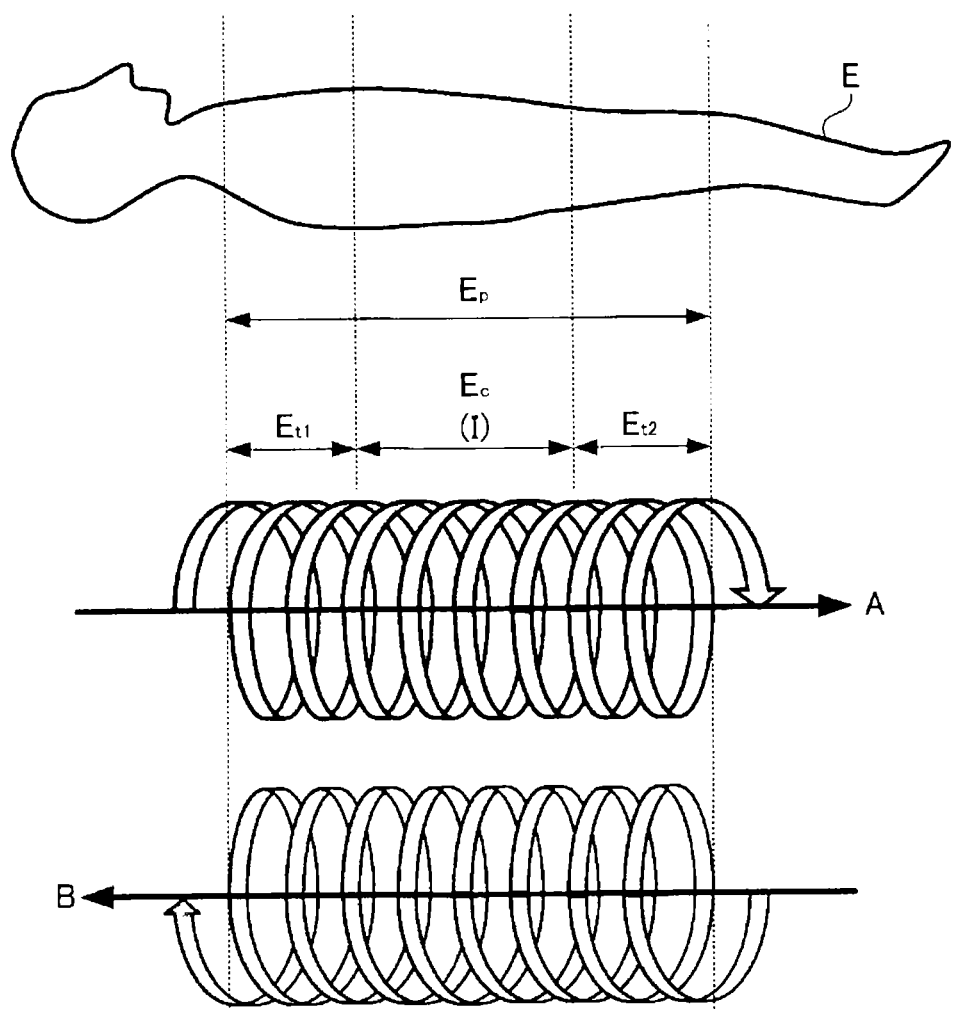
FIG. 3 is a schematic diagram for explaining an example of helical shuttle scanning.

Referring now to FIG. 3, helical shuttle scanning is described. Helical shuttle scanning is a method of performing helical scanning while the bed top 33 where the subject E is lying is being reciprocated in the first direction and the second direction. The helical scanning is a scanning method in which X-rays are irradiated in a spiral pattern around the subject E (see FIG. 3 in which the subject E and the spiral pattern are illustrated separately). Arrows A and B in FIG. 3 correspond to the arrows illustrated in FIG. 1. The arrow A indicates the direction in which the bed top 33 moves during the forward scan, while the arrow B indicates the direction in which the bed top 33 moves during the backward scan. In the case of helical shuttle scanning, synchronous trajectory scan is performed in which X-ray irradiation (and the movement of the bed) always starts from the same position for scans of different timings.

The couch drive unit 32 performs driving operation under the control of the controller 48 (the scan controller 42). The couch drive unit 32 moves the bed top 33 at a constant speed in a constant speed region $E_c$, which is set in an imaging range $E_p$ for the subject E. On the other hand, the couch drive unit 32 accelerates or decelerates the moving speed of the bed top 33 in a bed acceleration/deceleration region $E_{t1}$ ($E_{t2}$).

For example, when scan is performed in the first direction, the couch drive unit 32 accelerates the bed top 33 to achieve a predetermined moving speed in the bed acceleration/deceleration region $E_{t1}$. The couch drive unit 32 then moves the bed top 33 at the predetermined moving speed in the constant speed region $E_c$. After that, the couch drive unit 32 reduces the moving speed of the bed top 33 to stop it in the bed acceleration/deceleration region $E_{t2}$ to reverse the direction to move the bed top 33 to the direction of the arrow B. When scan is started in the second direction, the couch drive unit 32 accelerates the bed top 33 in the bed acceleration/deceleration region $E_{t2}$. By the helical scan with such reciprocating movement, a plurality of pieces of detection data can be acquired in the first direction and the second direction in the imaging range $E_p$. Note that, for example, the constant speed region $E_c$ falls into a range I corresponding to the region of interest of the subject E.

[Configuration of the Monitoring Unit 41]

Figure 4:
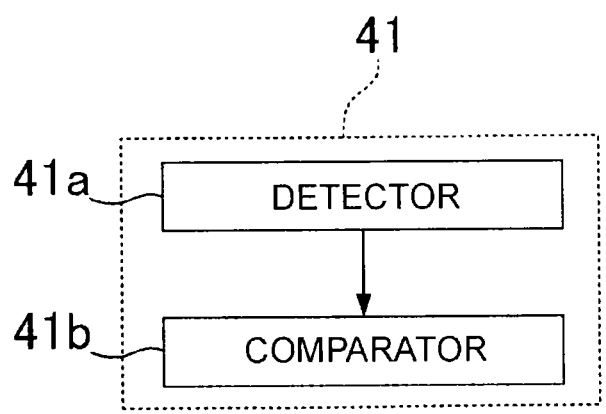
FIG. 4 is a block diagram of a monitoring unit of the first embodiment.
Figure 5:
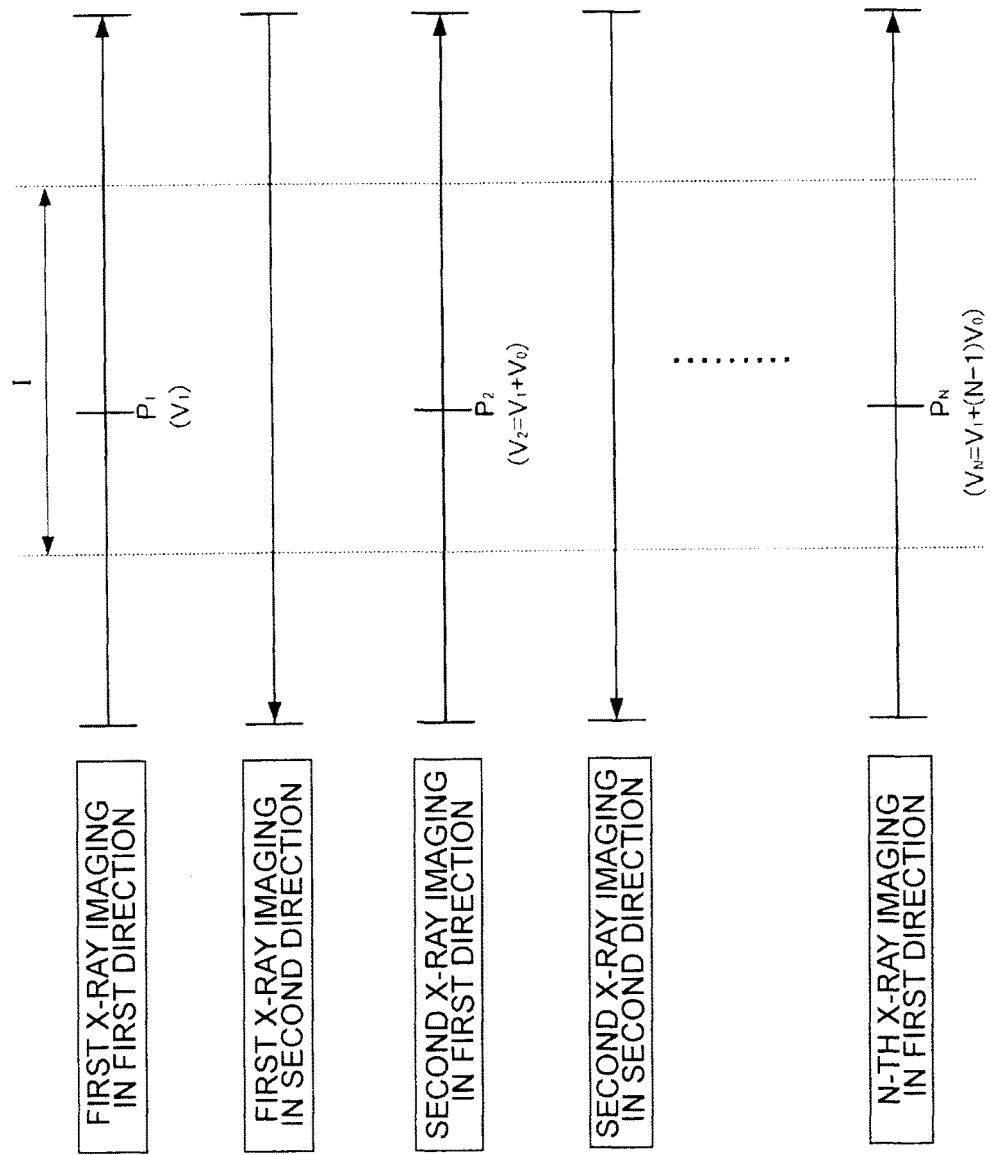
FIG. 5 is a diagram for supplementing the explanation of the monitoring unit of the first embodiment.

Next, with reference to FIGS. 4 and 5, the configuration of the monitoring unit 41 of the embodiment is described in detail. FIG. 4 is a block diagram of the configuration of the monitoring unit 41. FIG. 5 is a diagram illustrating the flow of helical shuttle scanning. In FIG. 5, the horizontal axis indicates the position of the bed top 33. Note that the number of reciprocating movements of the bed top 33 along with helical shuttle scanning is assumed to be N times (N>1).

The monitoring unit 41 includes a detector 41a and a comparator 41b.

In X-ray imaging in the first direction, the detector 41a detects the position of the bed top 33 when a predetermined number of views are acquired in the range I corresponding to the region of interest. In N times of reciprocating movements, that is, in N times of X-ray imaging in the first direction, the detector 41a of this embodiment detects the position of the bed top 33 when a predetermined number of views $V_k$ (k=1 to N) are acquired. As mentioned above, each view is associated with the position of the bed top 33 when the view is acquired. In the following, the position of the bed top 33 that is associated with the predetermined number of views $V_k$ is represented as position $P_k$ (k=1 to N). The position $P_k$ is a position in the body axis direction in FIG. 3. Information on the position of the bed top 33 detected is sent to the comparator 41b.

The predetermined number of views $V_k$ is a value that is used to monitor the reproducibility or repeatability of helical shuttle scanning. The predetermined number of views $V_k$ in this embodiment is determined by the sum of the predetermined number of views $V_1$ and the number of views according to the number of reciprocating movements.

From the number of views acquired in the first X-ray imaging in the first direction, any number of views (e.g., 20 views) is set in advance as the predetermined number of views $V_1$. The predetermined number of views $V_1$ is associated with a position $P_1$.

The number of views $V_0$ acquired during a single reciprocating movement may be determined in advance according to scanning conditions and the like. For example, the X-ray CT system 1 sets the scanning conditions based on an instruction input from the input unit 47 or the like to obtain 5 100 views in one reciprocating movement.

In this embodiment, the predetermined number of views $V_2$ acquired in the second X-ray imaging in the first direction is the sum (120 views) of the predetermined number of views $V_1$ (20 views) and the number of views $V_0$ acquired during one reciprocating movement. Similarly, the predetermined number of views $V_3$ acquired in the third X-ray imaging in the first direction is the sum (220 views) of the predetermined number of views $V_1$ (20 views) and the number of views $V_0$ acquired during two times of reciprocating movement. That is, the predetermined number of views $V_k$ can be represented as $V_1+(k-1)V_0$.

In other words, the detector 41a of the embodiment acquires a number of views $V_k$ in the k-th X-ray imaging by the use of the predetermined number of views $V_0$ acquired during one reciprocating movement as the number of views corresponding to each of (k−1) times of reciprocating movement.

The detector 41a counts the number of views acquired in the first X-ray imaging in the first direction, and detects the position $P_1$ of the bed top 33 that is associated with the view when a predetermined number of views $V_1$ (20 views) are acquired (see FIG. 5).

Thereafter, the detector 41a counts the number of views based on detection data sent from the data acquisition unit 14, and detects the position $P_2$ of the bed top 33 that is associated with the view when a predetermined number of views $V_2$ (=$V_1+V_0$) are acquired in the second X-ray imaging in the first direction (see FIG. 5).

Similarly, the detector 41a counts the number of views based on detection data sent from the data acquisition unit 14, and detects the position $P_N$ of the bed top 33 that is associated with the view when a predetermined number of views $V_N$ (=$V_1+(N-1)V_0$) are acquired in the N-th X-ray imaging in the first direction (see FIG. 5).

The comparator 41b compares the position $P_1$ of the bed top 33 detected in the first X-ray imaging in the first direction with the positions $P_k$ of the bed top 33 detected by the detector 41a in the k-th (k>1) X-ray imaging in the first direction, in which the sum of the predetermined number of views $V_1$ in the first X-ray imaging in the first direction and the number of views (k−1)$V_0$ corresponding to (k−1) times of reciprocating movement is obtained as the predetermined number of views $V_k$ in the N-th X-ray imaging.

Specifically, the comparator 41b compares the position $P_1$ detected in the first X-ray imaging in the first direction with the position $P_2$ detected in the second X-ray imaging in the first direction.

If the position $P_2$ is the same as the position $P_1$ (position $P_2$−position $P_1$=positional difference ΔP=0, see FIG. 5), it can be said that views (detection data) corresponding the predetermined number of views $V_1$ and views (detection data) corresponding to the predetermined number of views $V_2$ are acquired when the bed top 33 is located in the same position in the imaging range $E_p$ of helical shuttle scanning. Thus, by superimposing CT image data based on the detection data corresponding to these views, CT perfusion can be performed.

On the other hand, if the position $P_2$ is different from the position $P_1$ (positional difference ΔP≠0), it means that some sort of error occurs in helical scanning from the position $P_1$ to the position $P_2$. In the case of a comparison result such as this, it is unlikely that CT image data suitable for CT image superposition (CT perfusion) can be obtained even if helical shuttle scanning is continued.

The comparator 41b sends the comparison result to the scan controller 42. The comparator 41b compares the position $P_1$ with the position $P_k$ (k>1) for each reciprocating movement. That is, the positional difference ΔP can be represented by the following formula (1):

[Formula 1]

$$\Delta P = P_k - P_1 \qquad (1)$$

Note that, in the comparison of the positions $P_1$ and $P_k$ by the comparator 41b, they may not exactly coincide with each other. That is, the positional difference ΔP may have a predetermined margin (e.g., ±some millimeters) as long as it is within an allowable range where the reproducibility of helical shuttle scanning can be maintained.

The scan controller 42 performs control to continue or stop X-ray irradiation by the X-ray scanner based on the comparison result obtained by the comparator 41b.

Specifically, when the position $P_2$ is the same as the position $P_1$, the scan controller 42 controls the X-ray scanner to continue helical shuttle scanning. On the other hand, when the position $P_2$ is different from the position $P_1$, the scan controller 42 controls the X-ray scanner to stop helical shuttle scanning (stop X-ray irradiation by the X-ray generator 11).

As well as stopping X-ray irradiation, the scan controller 42 may stop the rotation of the rotating portion 10a. Besides, it takes a long time to start up the X-ray generator 11 when it is completely stopped. Accordingly, if the X-ray generator 11 is completely stopped, the test time is prolonged in the case of continuously performing another helical shuttle scanning or the like. Thus, the scan controller 42 may control the X-ray generator 11 to reduce the amount of X-ray irradiation based on the comparison result (positional difference ΔP≠0) obtained by the comparator 41b.

The display controller 44 of the embodiment provides error display on the display unit 46 based on the comparison result obtained by the comparator 41b.

Specifically, when the position $P_2$ is different from the position $P_1$, the display controller 44 displays on the display unit 46 a warning message indicating that an error has occurred in helical shuttle scanning.

The error display is not limited to the display of warning messages. The error display may be provided in any manner such as, for example, by flashing an icon displayed on the display unit 46, changing the window color, or the like as long as errors can be perceived. Alternatively, a warning message displayed on the display unit 46 may be accompanied (or replaced) by an alarm sound emitted from a warning unit (not illustrated).

<Operation>

Figure 6:
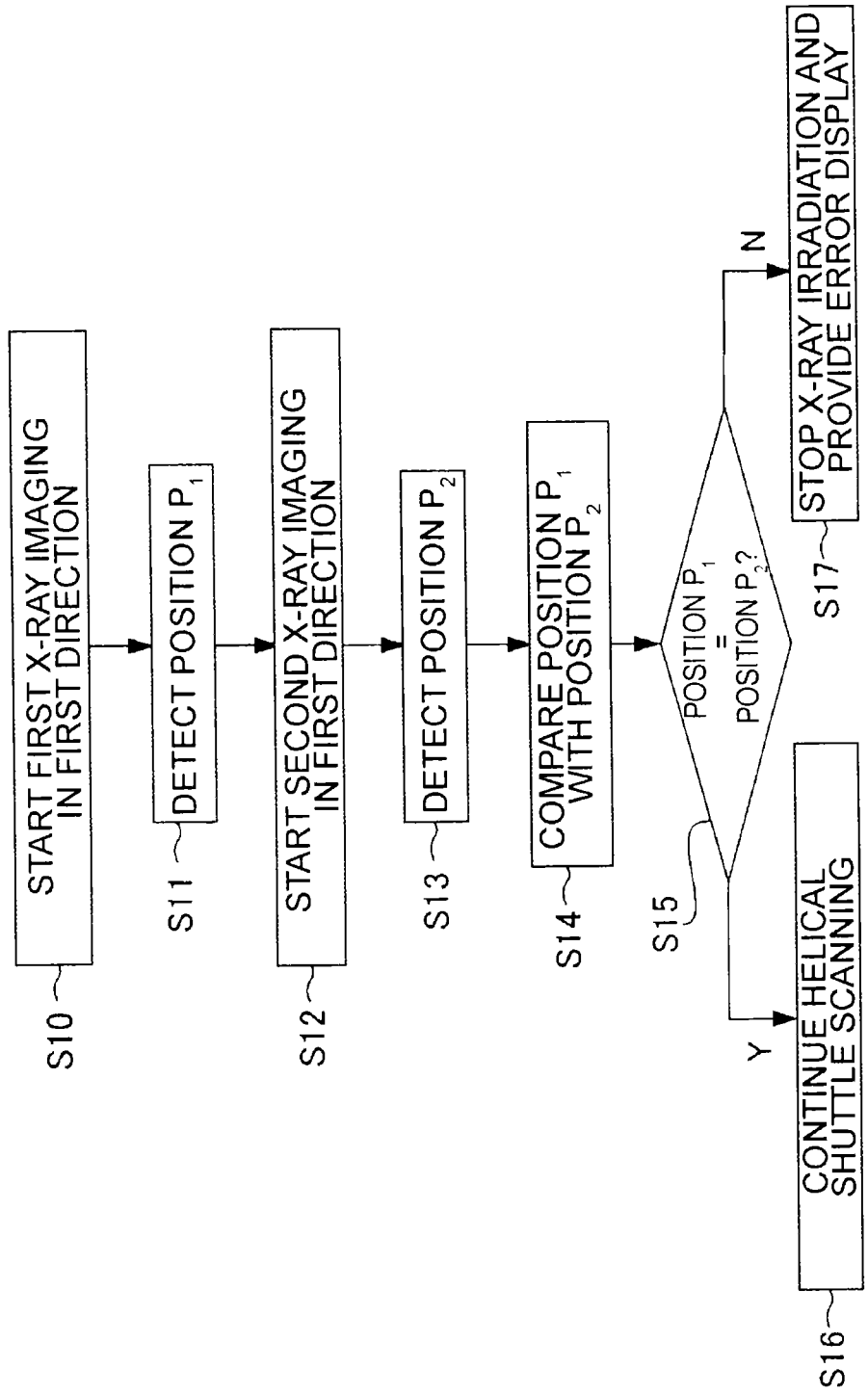
FIG. 6 is a flowchart of an outline of the operation of the X-ray CT system of the first embodiment.

Next, with reference to FIG. 6, a description is given of the operation of the X-ray CT system 1 in the embodiment. As the conditions of helical shuttle scanning, N times of reciprocating movement and the number of views $V_0$ acquired in one reciprocating movement are set in advance. In addition, the predetermined number of views $V_1$ is set in advance.

The scan controller 42 (the gantry-couch controller 18) starts helical scanning while moving the bed top 33 in the first direction with respect to the subject E (S10, the first X-ray imaging in the first direction). Detection data obtained in S10 is sent to the console device (the monitoring unit 41) in association with the position information of the bed top 33 for each view.

The detector 41a counts the number of views received, and detects the position $P_1$ of the bed top 33 when a predetermined number of views $V_1$ are acquired (S11). The scan controller 42 performs control based on the scanning conditions to continue the first reciprocating movement (helical scanning of the imaging range $E_p$ remaining in the first direction and helical scanning in the second direction).

After the completion of the first reciprocating movement, the scan controller 42 starts the second X-ray imaging in the first direction (S12).

In the second X-ray imaging in the first direction, when a predetermined number of views $V_2$ are acquired, the detector 41a detects the position $P_2$ of the bed top 33 that is associated with the view. The predetermined number of views $V_2$ is the sum of the number of views $V_1$ corresponding to the position $P_1$ of the bed top 33 and the number of views $V_0$ corresponding to one reciprocating movement (S13).

The comparator 41b compares the position $P_1$ of the bed top 33 detected in S11 with the position $P_2$ of the bed top 33 detected in S13 (S14). The comparison result is sent to the scan controller 42.

If the position $P_1$ and the position $P_2$ are the same (Y in S15), the scan controller 42 continues helical shuttle scanning based on the scanning conditions (S16).

On the other hand, if the position $P_1$ and the position $P_2$ are different (N in S15), the scan controller 42 stops X-ray irradiation by the X-ray scanner. In addition, the display controller 44 provides error display on the display unit 46 (S17).

The X-ray CT system 1 continues the above operation for the imaging range $E_p$ until the reciprocating movement of the bed top 33 is performed N times.

At this time, the detector 41a detects the position $P_k$ when a predetermined number of views $V_k$ are acquired in each X-ray imaging in the first direction. The comparator 41b compares between the position $P_1$ and the position $P_k$ detected in each X-ray imaging in the first direction. If the position $P_k$ is the same as the position $P_1$, the scan controller 42 continues helical shuttle scanning. If the position $P_k$ is different from the position $P_1$, the scan controller 42 stops X-ray irradiation by the X-ray scanner.

Thus, the X-ray CT system 1 of the embodiment can check whether X-ray imaging is performed in the same position for each of the predetermined number of views. That is, the X-ray CT system 1 of the embodiment monitors the positional reproducibility or repeatability of the bed top 33 based on the number of views.

An example is described above in which the reproducibility of helical shuttle scanning is monitored at a point in the range I corresponding to the region of interest (the position $P_k$ of the bed top 33 associated with the predetermined number of views $V_k$); however, it is not so limited. For example, the same process may be performed with respect to each view in the entire range I corresponding to the region of interest. In this manner, by monitoring the reproducibility in the entire range I corresponding to the region of interest, misalignment in the region of interest can be perceived more easily.

For example, the monitoring unit 41, the scan controller 42, the image processing unit 43, the display controller 44, and the controller 48 may be constituted of a processing unit (not illustrated) such as a central processing unit (CPU), a graphic processing unit (GPU), an application specific integrated circuit (ASIC) or the like, and a storage device (not illustrated) such as ROM, RAM, a hard disc drive (HDD) or the like. The storage device stores control programs for implementing the functions of each unit. Each of the programs stored in the storage device implements the functions of each unit when executed by the processing unit such as CPU.

The X-ray CT system 1 of the embodiment includes the bed top and the X-ray scanner. The X-ray scanner includes the X-ray generator 11 that performs X-ray imaging by scanning around the subject E that is lying on the bed top 33 and the X-ray detector 12. While the bed top 33 and the X-ray scanner are being relatively reciprocated in the first direction along the longitudinal direction of the bed top 33 and the second direction opposite thereto in the imaging range $E_p$ that includes the range I corresponding to the region of interest of the subject E, the X-ray scanner performs X-ray imaging in the position where it is moved to. The X-ray CT system 1 includes the detector 41a, the comparator 41b, and the scan controller 42. In the first X-ray imaging in the first direction, the detector 41a detects the position $P_k$ when a predetermined number of views $V_k$ are acquired in a range corresponding to the region of interest. The comparator 41b compares the position $P_1$ detected in the first X-ray imaging in the first direction with the position $P_k$ detected by the detector 41a when a predetermined number of views $V_k$ are acquired in the k-th (k>1) X-ray imaging in the first direction. The predetermined number of views $V_k$ is the sum of the predetermined number of views $V_1$ in the first X-ray imaging in the first direction and the number of views corresponding to (k−1) times of reciprocating movement. The scan controller 42 controls X-ray irradiation by the X-ray scanner based on the comparison result.

Specifically, the detector 41a obtains the predetermined number of views $V_k$ by using the number of views $V_0$ to be acquired during a single reciprocating movement set in advance as the number of views corresponding to (k−1) times of reciprocating movement.

In this manner, the detector 41a detects the position $P_k$ when a predetermined number of views $V_k$ are acquired in the range I corresponding to the region of interest for each forward movement (backward movement). Then, based on the comparison result obtained by the comparator 41b, the scan controller 42 controls X-ray irradiation by the X-ray scanner. With this, the X-ray CT system 1 of the embodiment can determine whether there is a displacement in the position $P_k$ for acquiring a predetermined number of views $V_k$ in the range I corresponding to the region of interest. That is, with the X-ray CT system 1 of the embodiment, it is possible to monitor the reproducibility of helical shuttle scanning based on arbitrary criteria (based on the number of views). Further, since X-ray irradiation is stopped when the reproducibility of helical shuttle scanning is poor, unnecessary radiation exposure can be reduced.

The X-ray CT system 1 of the embodiment further includes the display unit 46 and the display controller 44. The display controller 44 provides error display on the display unit 46 based on the comparison result.

By the error display provided based on the comparison result obtained by the comparator 41b (when the position $P_1 \neq$ the position $P_k$), the operator can easily determine whether displacement has occurred in the position $P_k$ for acquiring a predetermined number of views $V_k$ in the range I corresponding to the region of interest. That is, with the X-ray CT system 1 of the embodiment, it is possible to visually perceive a problem, if any, in the reproducibility of helical shuttle scanning.

The configuration described in this embodiment can be implemented by a control program. The control program for the X-ray CT system 1 of the embodiment causes a computer to implement the detection function, the comparison function, and the scan control function of the X-ray CT system 1 that includes the bed top 33 and the X-ray scanner including the X-ray generator 11 that performs X-ray imaging by scanning around the subject E lying on the bed top 33 and the X-ray detector 12, in which, while the bed top 33 and the X-ray scanner are being relatively reciprocated in the first direction along the longitudinal direction of the bed top 33 and the second direction opposite thereto in the imaging range $E_p$ that includes the range I corresponding to the region of interest of the subject E, the X-ray scanner performs X-ray imaging in the position where it is moved to. In X-ray imaging in the first direction, the detection function detects the position $P_k$ when a predetermined number of views $V_k$ are acquired in the range I corresponding to the region of interest. The comparison function compares the position $P_1$ detected in the first X-ray imaging in the first direction with the position $P_k$ detected when a predetermined number of views $V_k$ are acquired in the k-th (k>1) X-ray imaging in the first direction. The predetermined number of views $V_k$ is the sum of the predetermined number of views $V_1$ in the first X-ray imaging in the first direction and the number of views corresponding to (k−1) times of reciprocating movement. The scan control function controls X-ray irradiation by the X-ray scanner based on the comparison result.

In this manner, the detection function implemented by the control program detects the position $P_k$ when a predetermined number of views $V_k$ are acquired in the range I corresponding to the region of interest. Then, based on the comparison result obtained by the comparison function, the scan control function controls X-ray irradiation by the X-ray scanner. With this, by executing the control program of the embodiment, the X-ray CT system 1 can determine whether there is a displacement in the position $P_k$ for acquiring a predetermined number of views $V_k$ in the range I corresponding to the region of interest. That is, with the control program for the X-ray CT system 1 of the embodiment, it is possible to monitor the reproducibility of helical shuttle scanning based on arbitrary criteria (based on the number of views). Further, since X-ray irradiation is stopped when the reproducibility of helical shuttle scanning is poor, unnecessary radiation exposure can be reduced.

Second Embodiment

In the following, the configuration of the X-ray CT system 1 of a second embodiment is described referring to FIGS. 7 and 8. In this embodiment, an example is described in which the reproducibility of helical shuttle scanning is monitored with the use of measured values of the number of views. Regarding the same configuration and the like as in the first embodiment, a detailed description may not be provided here.

As in the first embodiment, the number of views to be acquired in one reciprocating movement (e.g., the number of views $V_0$) is set in advance as a scanning condition. However, the number of views $V_0$ may differ from the number of views $V_{total}$ actually acquired in one reciprocating movement (a difference may occur between the number of views $V_0$ and the number of views $V_{total}$).

For example, in helical shuttle scanning, X-ray imaging is performed also in the bed acceleration/deceleration region $E_{t1}$, ($E_{t2}$). Thus, the X-ray CT system 1 acquires detection data corresponding to a view taking into account the acceleration/deceleration curve in the bed acceleration/deceleration region $E_{t1}$, ($E_{t2}$). In general, an S-curve is used as the acceleration/deceleration curve to moderate the impact of reciprocating movement, and therefore error occurs in the calculation of time required for the acceleration and deceleration. Accordingly, error may occur in the number of views acquired during the acceleration and deceleration.

Further, in helical shuttle scanning performed by reciprocating the bed top 33, variation in the mechanical response of the bed top 33 and the like causes variation in detection data (variation in the number of views). The variation in the mechanical response of the bed top 33 refers to variation in the moving state of the bed top 33 based on differences in load distribution and weight caused by the body type of the subject E or the like. For example, if the bed top 33 is driven by a servo motor and the load on the servo motor is small (when the weight of the subject E placed on the bed top 33 is light), response at the start of movement of the bed top 33 is fast. On the other hand, when the load on the servo motor is large (when the subject E placed on the bed top 33 is heavy), response at the start of movement of the bed top 33 becomes slow. This machine response is a variation that cannot be perceived unless the bed top 33 is actually driven after the start of helical shuttle scanning. This variation may lead to errors in the number of views.

Therefore, the detector 41a of the embodiment acquires a predetermined number of views $V_k$ in the k-th X-ray imaging by the use of the number of views $V_{total}$ obtained in the first reciprocating movement as the number of views corresponding to (k−1) times of reciprocating movement.

Specifically, the X-ray CT system 1 starts helical shuttle scanning according to scanning conditions set in advance (e.g., N times of reciprocating movement and the number of views $V_0$ acquired in one reciprocating movement). It is assumed herein that the predetermined number of views $V_1$ is set to 20 views in advance.

In the same manner as in the first embodiment, the detector 41a counts the number of views acquired in the first X-ray imaging in the first direction. When a predetermined number of views $V_1$ (20 views) are acquired, the detector 41a detects the position $P_1$ of the bed top 33 that is associated with the view (see FIG. 7).

Further, by continuing to count the number of views, the detector 41a obtains the number of views $V_{go}$ actually acquired in the first X-ray imaging in the first direction and the number of views $V_{return}$ actually acquired in the first X-ray imaging in the second direction (see FIG. 7). Then, the detector 41a obtains the number of views $V_{total}$ corresponding to the sum of the number of views $V_{go}$ and the number of views $V_{return}$. The detector 41a replaces the number of views $V_0$ in the scanning conditions with the number of views $V_{total}$.

After that, the detector 41a counts the number of views based on detection data sent from the data acquisition unit 14. When a predetermined number of views $V_2$ are acquired, the detector 41a detects the position $P_2$ of the bed top 33 that is associated with the view (see FIG. 7). In the embodiment, the predetermined number of views $V_2$ corresponds to the sum of the predetermined number of views $V_1$ in the first X-ray imaging in the first direction and the number of views $V_{total}$ as a measured value.

Similarly, the detector 41a counts the number of views based on detection data sent from the data acquisition unit 14. When a predetermined number of views $V_N$ (=$V_1$+(N−1)$V_{total}$) are acquired in the N-th X-ray imaging in the first direction, the detector 41a detects the position $P_N$ of the bed top 33 that is associated with the view (see FIG. 7).

<Operation>

Next, with reference to FIG. 8, a description is given of the operation of the X-ray CT system 1 in the embodiment. As the conditions of helical shuttle scanning, N times of reciprocating movement and the number of views $V_0$ acquired in one reciprocating movement are set in advance. In addition, the predetermined number of views $V_1$ is set in advance.

The scan controller 42 (the gantry-couch controller 18) starts helical scanning while moving the bed top 33 in the first direction with respect to the subject E (S20, the first X-ray imaging in the first direction). Detection data obtained in S20 is sent to the console device (the monitoring unit 41) in association with the position information of the bed top 33 for each view.

The detector 41a counts the number of views received, and detects the position $P_1$ of the bed top 33 when a predetermined number of views $V_1$ are acquired (S21). The scan controller 42 performs control based on the scanning conditions to continue the first reciprocating movement (helical scanning of the imaging range $E_p$ remaining in the first direction and helical scanning in the second direction).

The detector 41a obtains the number of views $V_{total}$ (=$V_{go}$+$V_{return}$) in the first reciprocating movement (S22).

The detector 41a replaces the number of views $V_0$ in the scanning conditions with the number of views $V_{total}$ (S23).

After the completion of the first reciprocating movement, the scan controller 42 starts the second X-ray imaging in the first direction (S24).

In the second X-ray imaging in the first direction, when a predetermined number of views $V_2$ are acquired, the detector 41a detects the position $P_2$ of the bed top 33 that is associated with the view. The predetermined number of views $V_2$ is the sum of the number of views $V_1$ corresponding to the position $P_1$ of the bed top 33 and the number of views $V_{total}$ obtained in S22 (S25).

The comparator 41b compares the position $P_1$ of the bed top 33 detected in S21 with the position $P_2$ of the bed top 33 detected in S25 (S26). The comparison result is sent to the scan controller 42.

If the position $P_1$ and the position $P_2$ are the same (Y in S27), the scan controller 42 continues helical shuttle scanning based on the scanning conditions (S28).

On the other hand, if the position $P_1$ and the position $P_2$ are different (N in S27), the scan controller 42 stops X-ray irradiation by the X-ray scanner. In addition, the display controller 44 provides error display on the display unit 46 (S29).

The X-ray CT system 1 continues the above operation for the imaging range $E_p$ until the reciprocating movement of the bed top 33 is performed N times.

At this time, the detector 41a detects the position $P_k$ when a predetermined number of views $V_k$ are acquired in each X-ray imaging in the first direction. The comparator 41b compares between the position $P_1$ and the position $P_k$ detected in each X-ray imaging in the first direction. If the position $P_k$ is the same as the position $P_1$, the scan controller 42 continues helical shuttle scanning. If the position $P_k$ is different from the position $P_1$, the scan controller 42 stops X-ray irradiation by the X-ray scanner.

In this embodiment, the detector 41a of the X-ray CT system 1 acquires a predetermined number of views $V_k$ by the use of the number of views $V_{total}$ obtained in the first reciprocating movement as the number of views corresponding to (k−1) times of reciprocating movement.

Thus, the detector 41a acquires a predetermined number of views $V_k$ in the k-th X-ray imaging by the use of the number of views $V_{total}$ obtained in the first reciprocating movement. The number of views $V_{total}$ is a measured value that takes into account the influence of the body type of the subject E. That is, with the X-ray CT system 1 of the embodiment, it is possible to monitor the reproducibility of helical shuttle scanning in consideration of an error due to variation in the mechanical response and calculation error.

Third Embodiment

In the following, the configuration of the X-ray CT system 1 of a third embodiment is described referring to FIGS. 9 and 10. In this embodiment, an example is described in which the reproducibility of helical shuttle scanning is monitored based on the number of views detected with reference to a predetermined position. Regarding the same configuration and the like as in the first and the second embodiments, a detailed description may not be provided here.

The monitoring unit 41 of the embodiment monitors the reproducibility of helical shuttle scanning at a predetermined position C in the range I corresponding to the region of interest of the subject E. The monitoring unit 41 includes the detector 41a and the comparator 41b.

In X-ray imaging in the first direction, the detector 41a of the embodiment detects the number of views acquired at a predetermined position C in the range I corresponding to the region of interest. Specifically, in the first X-ray imaging in the first direction, the detector 41a detects the number of views $V'_1$ when the bed top 33 reaches the predetermined position C. Further, in the k-th X-ray imaging in the first direction, the detector 41a detects the number of views $V'_k$ (k=1 to N) when the bed top 33 reaches the predetermined position C. The number of views detected is sent to the comparator 41b.

As the predetermined position C, an arbitrary position is set in advance in the range I corresponding to the region of interest.

As in the first embodiment, the number of views $V_0$ to be acquired during a single reciprocating movement may be determined in advance according to scanning conditions. In this case, the number of views acquired during k times of reciprocating movement can be represented as the number of views $kV_0$.

In the first X-ray imaging in the first direction, the detector 41a detects the number of views $V'_1$ at the predetermined position C (see FIG. 9).

Then, the detector 41a continues to count the number of views based on detection data sent from the data acquisition unit 14, and detects the number of views $V'_2$ at the predetermined position C in the second X-ray imaging in the first direction (see FIG. 9).

Similarly, the detector 41a continues to count the number of views based on detection data sent from the data acquisition unit 14, and detects the number of views $V'_N$ acquired at the predetermined position C in the N-th X-ray imaging in the first direction (see FIG. 9).

The comparator 41b compares the number of views $V'_1$ detected in the first X-ray imaging in the first direction with the number of views $V'_k$ detected in the k-th (k>1) X-ray imaging in the first direction. The difference between the number of views $V'_1$ and the number of views $V'_k$ is represented as the difference $\Delta V_k$ (k=2 to N).

Specifically, the comparator 41b compares the number of views $V'_1$ detected at the predetermined position C in the first X-ray imaging in the first direction with the number of views $V'_2$ detected at the predetermined position C in the second X-ray imaging in the first direction.

When the difference $\Delta V_2$ between the number of views $V'_1$ and the number of views $V'_2$ is $V_0$, it can be said that views (detection data) corresponding to the number of views $V'_2$ are acquired after one reciprocating movement for views (detection data) corresponding to the number of views $V'_1$ (acquired by photographing the same position in the imaging range $E_p$). In other words, the periodicity of helical shuttle scanning is maintained. Thus, by superimposing CT image data based on the detection data corresponding to these views, CT perfusion can be performed.

On the other hand, if the difference $\Delta V_2$ between the number of views $V'_1$ and the number of views $V'_2$ is other than $V_0$, it means that some sort of error occurs in helical scanning from the predetermined position C in the first X-ray imaging in the first direction to the predetermined position C in the second X-ray imaging in the first direction. In other words, the periodicity of helical shuttle scanning is broken. In the case of a comparison result such as this, it is unlikely that CT image data suitable for CT image superposition (CT perfusion) can be obtained even if helical shuttle scanning is continued.

The comparator 41b sends the comparison result to the scan controller 42. The comparator 41b compares the number of views $V'_1$ with the number of views $V'_k$ (k>1) for each reciprocating movement. That is, the difference $\Delta V_k$ can be represented by the following formula (2):

[Formula 2]

$$\Delta V_k = V'_k - V'_1 \quad (2)$$

In this embodiment, the comparator 41b performs a comparison based on the number of views $V_0$ to be acquired during a single reciprocating movement set in advance. For example, the comparator 41b compares the difference $\Delta V_N$ between the number of views $V'_1$ and the number of views $V'_N$ detected at the predetermined position C in the N-th X-ray imaging in the first direction with the number of views (N−1) $V_0$. In other words, the comparator 41b of the embodiment compares the difference $\Delta V_k$ with the number of views (k−1)$V_0$.

Note that, in the comparison of the number of views $V'_1$ and the number of views $V'_k$ by the comparator 41b, the difference $\Delta V_k$ may not exactly match the number of views (k−1)$V_0$. That is, the difference $\Delta V_k$ may have a predetermined margin (e.g., ±some views) as long as it is within an allowable range where the reproducibility of helical shuttle scanning can be maintained.

<Operation>

Next, with reference to FIG. 10, a description is given of the operation of the X-ray CT system 1 in the embodiment. As the conditions of helical shuttle scanning, N times of reciprocating movement and the number of views $V_0$ acquired in one reciprocating movement are set in advance.

The scan controller 42 (the gantry-couch controller 18) starts helical scanning while moving the bed top 33 in the first direction with respect to the subject E (S30, the first X-ray imaging in the first direction). Detection data obtained in S30 is sent to the console device (the monitoring unit 41) in association with the position information of the bed top 33 for each view.

The detector 41a detects the number of views $V'_1$ at the predetermined position C (S31). The scan controller 42 performs control based on the scanning conditions to continue the first reciprocating movement (helical scanning of the imaging range $E_p$ remaining in the first direction and helical scanning in the second direction).

After the completion of the first reciprocating movement, the scan controller 42 starts the second X-ray imaging in the first direction (S32).

In the second X-ray imaging in the first direction, the detector 41a detects the number of views $V'_2$ at the predetermined position C (S33).

The comparator 41b compares the number of views $V'_1$ detected in S31 with the number of views $V'_2$ detected in S33 (S34). The comparison result is sent to the scan controller 42.

If the difference $\Delta V_2$ between the number of views $V'_1$ and the number of views $V'_2$ is $V_0$ (Y in S35), the scan controller 42 continues helical shuttle scanning based on the scanning conditions (S36).

On the other hand, if the difference $\Delta V_2$ between the number of views $V'_1$ and the number of views $V'_2$ is other than $V_0$ (N in S35), the scan controller 42 stops X-ray irradiation by the X-ray scanner. In addition, the display controller 44 provides error display on the display unit 46 (S37).

The X-ray CT system 1 continues the above operation for the imaging range $E_p$ until the reciprocating movement of the bed top 33 is performed N times.

At this time, the detector 41a detects the number of views $V'_k$ acquired at the predetermined position C in each X-ray imaging in the first direction. The comparator 41b compares the number of views $V'_1$ with the number of views $V'_k$ acquired at the predetermined position C in each X-ray imaging in the first direction. When the difference $\Delta V_k$ between the number of views $V'_1$ and the number of views $V'_k$ is (k−1)$V_0$, the scan controller 42 continues helical shuttle scanning. If the difference $\Delta V_k$ between the number of views $V'_1$ and the number of views $V'_k$ is different from (k−1)$V_0$, the scan controller 42 stops X-ray irradiation by the X-ray scanner.

Thus, the X-ray CT system 1 of the embodiment can check whether periodicity is maintained at a defined location (predetermined position C) in each reciprocating movement. That is, the X-ray CT system 1 of the embodiment monitors the periodicity of helical shuttle scanning (periodicity of views) based on a reference position.

The X-ray CT system 1 of the embodiment includes the bed top and the X-ray scanner. The X-ray scanner includes the X-ray generator 11 that performs X-ray imaging by scanning around the subject E that is lying on the bed top 33 and the X-ray detector 12. While the bed top 33 and the X-ray scanner are being relatively reciprocated in the first direction along the longitudinal direction of the bed top 33 and the second direction opposite thereto in the imaging range $E_p$ that includes the range I corresponding to the region of interest of the subject E, the X-ray scanner performs X-ray imaging in the position where it is moved to. The X-ray CT system 1 includes the detector 41a, the comparator 41b, and the scan controller 42. In X-ray imaging in the first direction, the detector 41a detects the number of views $V'_k$ acquired at the predetermined position C in the range I corresponding to the region of interest. The comparator 41b compares the number of views $V'_1$ detected in the first X-ray imaging in the first direction with the number of views $V'_k$ detected in the k-th (k>1) X-ray imaging in the first direction. The scan controller 42 controls X-ray irradiation by the X-ray scanner based on the comparison result.

Specifically, based on the number of views $V_0$ to be acquired during a single reciprocating movement set in advance, the comparator 41b compares the number of views $V'_1$ detected in the first X-ray imaging in the first direction with the number of views $V'_k$ detected in the k-th X-ray imaging in the first direction.

In this manner, the detector 41a detects the number of views $V'_k$ at the predetermined position C in the range I corresponding to the region of interest. Then, based on the comparison result obtained by the comparator 41b, the scan controller 42 controls X-ray irradiation by the X-ray scanner. With this, the X-ray CT system 1 of the embodiment can determine whether the periodicity of helical shuttle scanning is maintained in the range I corresponding to the region of interest. That is, with the X-ray CT system 1 of the embodiment, it is possible to monitor the reproducibility of helical shuttle scanning based on arbitrary criteria (based on a position). Further, since X-ray irradiation is stopped when the reproducibility of helical shuttle scanning is poor, unnecessary radiation exposure can be reduced.

The configuration described in this embodiment can be implemented by a control program. The control program for the X-ray CT system 1 of the embodiment causes a computer to implement the detection function, the comparison function, and the scan control function of the X-ray CT system 1 that includes the bed top 33 and the X-ray scanner including the X-ray generator 11 that performs X-ray imaging by scanning around the subject E lying on the bed top 33 and the X-ray detector 12, in which, while the bed top 33 and the X-ray scanner are being relatively reciprocated in the first direction along the longitudinal direction of the bed top 33 and the second direction opposite thereto in the imaging range $E_p$ that includes the range I corresponding to the region of interest of the subject E, the X-ray scanner performs X-ray imaging in the position where it is moved to. In X-ray imaging in the first direction, the detection function detects the number of views $V'_k$ acquired at the predetermined position C in the range I corresponding to the region of interest. The comparison function compares the number of views $V'_1$ detected in the first X-ray imaging in the first direction with the number of views $V'_k$ detected in the k-th (k>1) X-ray imaging in the first direction. The scan control function controls X-ray irradiation by the X-ray scanner based on the comparison result.

In this manner, the detection function implemented by the control program detects the number of views $V'_k$ at the predetermined position C in the range I corresponding to the region of interest. Then, based on the comparison result obtained by the comparison function, the scan control function controls X-ray irradiation by the X-ray scanner. With this, by executing the control program of the embodiment, the X-ray CT system 1 can determine whether the periodicity of helical shuttle scanning is maintained in the range I corresponding to the region of interest. That is, with the control program for the X-ray CT system 1 of the embodiment, it is possible to monitor the reproducibility of helical shuttle scanning based on arbitrary criteria (based on the position). Further, since X-ray irradiation is stopped when the reproducibility of helical shuttle scanning is poor, unnecessary radiation exposure can be reduced.

Fourth Embodiment

In the following, the configuration of the X-ray CT system 1 of a fourth embodiment is described referring to FIGS. 11 and 12. In this embodiment, an example is described in which the reproducibility of helical shuttle scanning is monitored with the use of measured values of the number of views in the configuration of the third embodiment. Regarding the same configuration and the like as in the first to third embodiments, a detailed description may not be provided here.

As in the third embodiment, the number of views to be acquired in one reciprocating movement (e.g., the number of views $V_0$) is set in advance as a scanning condition. However, as has already been described in the second embodiment, the number of views $V_0$ may differ from the number of views $V_{total}$ actually acquired in one reciprocating movement due to variation in the mechanical response and calculation error.

Therefore, the comparator 41b of the embodiment compares the number of views $V'_1$ detected in the first X-ray imaging in the first direction with the number of views $V'_k$ detected in the k-th X-ray imaging in the first direction based on the number of views $V_{total}$ acquired in the first reciprocating movement.

Specifically, the X-ray CT system 1 starts helical shuttle scanning according to scanning conditions set in advance (e.g., N times of reciprocating movement and the number of views $V_0$ acquired in one reciprocating movement).

As in the third embodiment, the detector 41a detects the number of views $V'_1$ at the predetermined position C in the first X-ray imaging in the first direction (see FIG. 11).

Further, by continuing to count the number of views, the detector 41a acquires the number of views $V_{go}$ actually acquired in the first X-ray imaging in the first direction and the number of views $V_{return}$ actually acquired in the first X-ray imaging in the second direction (see FIG. 11). Then, the detector 41a obtains the number of views $V_{total}$ corresponding to the sum of the number of views $V_{go}$ and the number of views $V_{return}$. The detector 41a replaces the number of views $V_0$ in the scanning conditions with the number of views $V_{total}$.

Then, the detector 41a continues to count the number of views based on detection data sent from the data acquisition unit 14, and detects the number of views $V'_2$ at the predetermined position C in the second X-ray imaging in the first direction (see FIG. 11).

Similarly, the detector 41a continues to count the number of views based on detection data sent from the data acquisition unit 14, and detects the number of views $V'_N$ acquired at the predetermined position C in the N-th X-ray imaging in the first direction (see FIG. 11).

The comparator 41b compares the number of views $V'_1$ acquired in the first X-ray imaging with the number of views $V'_2$ acquired in the second X-ray imaging based on the number of views $V_{total}$ (measured value) acquired in the first reciprocating movement.

When the difference $\Delta V_2$ between the number of views $V'_1$ and the number of views $V'_2$ is the number of views $V_{total}$, it is assumed that views (detection data) corresponding to the number of views $V'_2$ is acquired after one reciprocating movement for views (detection data) corresponding to the number of views $V'_1$ (acquired by photographing the same position in the imaging range $E_p$). In other words, the periodicity of helical shuttle scanning is maintained. Thus, by superimposing CT image data based on the detection data corresponding to these views, CT perfusion can be performed.

On the other hand, if the difference $\Delta V_2$ between the number of views $V'_1$ and the number of views $V'_2$ is other than the number of views $V_{total}$, it means that some sort of error occurs in helical scanning from the predetermined position C in the first X-ray imaging in the first direction to the predetermined position C in the second X-ray imaging in the first direction. In other words, the periodicity of helical shuttle scanning is broken. In the case of a comparison result such as this, it is unlikely that CT image data suitable for CT image superposition (CT perfusion) can be obtained even if helical shuttle scanning is continued.

The comparator 41b sends the comparison result to the scan controller 42. The comparator 41b compares the number of views $V'_1$ with the number of views $V'_k$ ((k>1) for each reciprocating movement. In the embodiment, the comparator 41b performs a comparison based on the number of views $V_{total}$ as a measured value. For example, the comparator 41b compares the difference $\Delta V_N$ between the number of views $V'_1$ and the number of views $V'_N$ detected at the predetermined position C in the N-th X-ray imaging in the first direction with the number of views $(N-1)V_{total}$. In other words, the comparator 41b of the embodiment compares the difference $\Delta V_k$ with the number of views $(k-1)V_{total}$. With the use of measured values, it is possible to reduce the influence of variation in the mechanical response and calculation error.

<Operation>

Next, with reference to FIG. 12, a description is given of the operation of the X-ray CT system 1 in the embodiment. As the conditions of helical shuttle scanning, N times of reciprocating movement and the number of views $V_0$ acquired in one reciprocating movement are set in advance.

The scan controller 42 (the gantry-couch controller 18) starts helical scanning while moving the bed top 33 in the first direction with respect to the subject E (S40, the first X-ray imaging in the first direction). Detection data obtained in S40 is sent to the console device (the monitoring unit 41) in association with the position information of the bed top 33 for each view.

The detector 41a detects the number of views $V'_1$ at the predetermined position C (S41). The scan controller 42 performs control based on the scanning conditions to continue the first reciprocating movement (helical scanning of the imaging range $E_p$ remaining in the first direction and helical scanning in the second direction).

The detector 41a obtains the number of views $V_{total}$ (=$V_{go}+V_{return}$) in the first reciprocating movement (S42).

The detector 41a replaces the number of views $V_0$ in the scanning conditions with the number of views $V_{total}$ (S43).

After the completion of the first reciprocating movement, the scan controller 42 starts the second X-ray imaging in the first direction (S44).

In the second X-ray imaging in the first direction, the detector 41a detects the number of views $V'_2$ at the predetermined position C (S45).

The comparator 41b compares the number of views $V'_1$ detected in S41 with the number of views $V'_2$ detected in S45 (S46). The comparison result is sent to the scan controller 42.

If the difference $\Delta V_2$ between the number of views $V'_1$ and the number of views $V'_2$ is $V_{total}$ (Y in S47), the scan controller 42 continues helical shuttle scanning based on the scanning conditions (S48).

On the other hand, if the difference $\Delta V_2$ between the number of views $V'_1$ and the number of views $V'_2$ is other than $V_{total}$ (N in S47), the scan controller 42 stops X-ray irradiation by the X-ray scanner. In addition, the display controller 44 provides error display on the display unit 46 (S49).

The X-ray CT system 1 continues the above operation for the imaging range $E_p$ until the reciprocating movement of the bed top 33 is performed N times.

At this time, the detector 41a detects the number of views $V'_k$ acquired at the predetermined position C in each X-ray imaging in the first direction. The comparator 41b compares the number of views with the number of views $V'_k$ acquired at the predetermined position C in each X-ray imaging in the first direction. When the difference $\Delta V_k$ between the number of views and the number of views $V'_k$ is $(k-1)V_{total}$, the scan controller 42 continues helical shuttle scanning. If the difference $\Delta V_k$ between the number of views $V'$ and the number of views $V'_k$ is different from $(k-1)V_{total}$, the scan controller 42 stops X-ray irradiation by the X-ray scanner.

In the X-ray CT system 1 of the embodiment, the comparator 41b compares the number of views detected in the first X-ray imaging in the first direction with the number of views $V'_k$ detected in the k-th X-ray imaging in the first direction based on the number of views $V_{total}$ acquired in the first reciprocating movement.

In this manner, the comparator 41b compares the numbers of views acquired at the predetermined position C using the number of views $V_{total}$ acquired in the first reciprocating movement. The number of views $V_{total}$ is a measured value that takes into account the influence of the body type of the subject E. That is, with the X-ray CT system 1 of the embodiment, it is possible to monitor the reproducibility of helical shuttle scanning in consideration of an error due to variation in the mechanical response and calculation error.

Modification

In the above embodiments, the bed top 33 is described as being moved; however, this is by way of example and not limitation. For example, helical shuttle scanning can be performed by moving the gantry device 10 with respect to the bed top 33 that is fixed. Specifically, while relatively reciprocating the bed top 33 and the X-ray scanner in the first direction along the longitudinal direction of the bed top 33 and in the second direction opposite thereto in an imaging range including a range corresponding to the region of interest of the subject E, the controller 48 controls the X-ray scanner to perform X-ray imaging in the position where it is moved to. When the gantry device 10 is moved, the position of the gantry device 10 can be used in place of the position of the bed top 33 (predetermined position) described above.

With the X-ray CT system of at least one of the embodiments described above, it is possible to monitor the reproducibility of helical shuttle scanning based on arbitrary criteria (based on the number of views or a position). Further, since X-ray irradiation is stopped when the reproducibility of helical shuttle scanning is poor, unnecessary radiation exposure can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT system, comprising:
   an X-ray scanner including an X-ray generator that performs X-ray imaging by scanning around a subject that is placed on a bed top and an X-ray detector, wherein the X-ray seamier is configured to perform X-ray imaging while the bed top and the X-ray scanner are being reciprocated relative to each other in a first direction along a longitudinal direction of the bed top and a second direction opposite to the first direction, the X-ray CT system further comprising a comparator configured to compare positions of the bed top when predetermined numbers of views are acquired in a plurality of times of X-ray imaging in the first direction or in a plurality of times of X-ray imaging in the second direction.

2. The X-ray CT system of claim 1, further comprising a scan controller configured to control X-ray irradiation by the X-ray scanner based on a comparison result obtained by the comparator.

3. An X-ray CT system, comprising:
a bed top; and
an X-ray scanner including an X-ray generator that performs X-ray imaging by scanning around a subject that is placed on the bed top and an X-ray detector, wherein the X-ray scanner is configured to perform X-ray imaging at a position where the X-ray scanner is moved while the bed top and the X-ray scanner are being relatively reciprocated in a first direction along a longitudinal direction of the bed top and a second direction opposite to the first direction in an imaging range that includes a range corresponding to a region of interest of the subject, the X-ray CT system further comprising:
a detector configured to detect the position when a predetermined number of views are acquired in the range corresponding to the region of interest in X-ray imaging in the first direction for each reciprocating movement;
a comparator configured to compare the position detected in first X-ray imaging in the first direction with the position detected by the detector when the predetermined number of views are acquired in a k-th (k>1) X-ray imaging in the first direction, wherein the predetermined number of views is a sum of a predetermined number of views in the first X-ray imaging in the first direction and a number of views corresponding to (k−1) times of reciprocating movement; and
a scan controller configured to control X-ray irradiation by the X-ray scanner based on a comparison result.

4. The X-ray CT system of claim 3, wherein the detector is configured to acquire the predetermined number of views in the k-th X-ray imaging using a number of views to be acquired in one reciprocating movement set in advance as the number of views corresponding to (k−1) times of reciprocating movement.

5. The X-ray CT system of claim 3, wherein the detector is configured to acquire the predetermined number of views in the k-th X-ray imaging using a number of views acquired in the first reciprocating movement as the number of views corresponding to (k−1) times of reciprocating movement.

6. The X-ray CT system of claim 3, wherein the scan controller is configured to perform control to stop X-ray irradiation by the X-ray scanner when the comparison result is out of an allowable range.

7. The X-ray CT system of claim 3, further comprising:
a display; and
a display controller configured to provide error display on the display based on the comparison result.

8. An X-ray CT system, comprising:
an X-ray scanner including an X-ray generator that performs X-ray imaging by scanning around a subject that is placed on a bed top and an X-ray detector, wherein the X-ray scanner is configured to perform X-ray imaging while the bed and the X-ray scanner are being reciprocated relative to each other in a first direction along a longitudinal direction of the bed top and a second direction opposite to the first direction, the X-ray CT system further comprising a comparator configured to compare numbers of views acquired at a predetermined position in a plurality of times of X-ray imaging in the first direction or in a plurality of times of X-ray imaging in the second direction.

9. The X-ray CT system of claim 8, further comprising a scan controller configured to control X-ray irradiation by the X-ray scanner based on a comparison result obtained by the comparator.

10. An X-ray CT system, comprising:
a bed top, and
an X-ray scanner including an X-ray generator that performs X-ray imaging by scanning around a subject that is placed on the bed top and an X-ray detector, wherein the X-ray scanner is configured to perform X-ray imaging at a position where the X-ray scanner is moved while the bed top and the X-ray scanner are being relatively reciprocated in a first direction along a longitudinal direction of the bed top and a second direction opposite to the first direction in an imaging range that includes a range corresponding to a region of interest of the subject, the X-ray CT system further comprising:
a detector configured to detect a number of views acquired at a predetermined position in the range corresponding to the region of interest in X-ray imaging in the first direction for each reciprocating movement;
a comparator configured to compare a number of views detected in first X-ray imaging in the first direction with a number of views detected in k-th (k>1) X-ray imaging in the first direction; and
a scan controller configured to control X-ray irradiation by the X-ray scanner based on a comparison result.

11. The X-ray CT system of claim 10, wherein the comparator is configured to compare the number of views detected in the first X-ray imaging in the first direction with the number of views detected in the k-th X-ray imaging in the first direction based on a number of views to be acquired in one reciprocating movement set in advance.

12. The X-ray CT system of claim 10, wherein the comparator is configured to compare the number of views detected in the first X-ray imaging in the first direction with the number of views detected in the k-th X-ray imaging in the first direction based on a number of views acquired in first reciprocating movement.

13. The X-ray CT system of claim 10, wherein the scan controller is configured to perform control to stop X-ray irradiation by the X-ray scanner when the comparison result is out of an allowable range.

14. The X-ray CT system of claim 10, further comprising:
a display; and
a display controller configured to provide error display on the display based on the comparison result.

* * * * *